US012290692B2

(12) United States Patent
Min et al.

(10) Patent No.: US 12,290,692 B2
(45) Date of Patent: May 6, 2025

(54) VENTRICULAR FAR-FIELD SENSING TO GUIDE ATRIAL LEADLESS PACEMAKER AND BEYOND

(71) Applicant: Pacesetter, Inc., Sylmar, CA (US)

(72) Inventors: Xiaoyi Min, Santa Rosa Valley, CA (US); Weiqun Yang, Cupertino, CA (US); Benjamin T. Persson, Saratoga, CA (US); Nima Badie, Berkeley, CA (US); Kyungmoo Ryu, Palmdale, CA (US); Gabriel Mouchawar, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 18/440,703

(22) Filed: Feb. 13, 2024

(65) Prior Publication Data
US 2024/0181265 A1    Jun. 6, 2024

Related U.S. Application Data

(62) Division of application No. 17/321,014, filed on May 14, 2021, now Pat. No. 11,931,590.
(Continued)

(51) Int. Cl.
*A61N 1/37* (2006.01)
*A61N 1/02* (2006.01)
(Continued)

(52) U.S. Cl.
CPC ......... *A61N 1/37288* (2013.01); *A61N 1/025* (2013.01); *A61N 1/36507* (2013.01);
(Continued)

(58) Field of Classification Search
CPC .... A61B 2560/0204; A61B 2562/0219; A61B 2562/0223; A61B 2562/0247;
(Continued)

(56) References Cited

U.S. PATENT DOCUMENTS 8,386,024 B2    2/2013    Gunderson et al.
8,774,909 B2    7/2014    Patel
(Continued)

FOREIGN PATENT DOCUMENTS

EP    1549213 B1    8/2007
EP    2364107 B1    9/2016

OTHER PUBLICATIONS

Restriction Requirement dated Mar. 3, 2023, U.S. Appl. No. 17/321,014, filed May 14, 2021.
(Continued)

*Primary Examiner* — Amanda K Hulbert
(74) *Attorney, Agent, or Firm* — Pearl Cohen Zedek Latzer Baratz LLP

(57) ABSTRACT

Described herein are methods for use with an implantable system including at least an atrial leadless pacemaker (aLP). Also described herein are specific implementations of an aLP, as well as implantable systems including an aLP. In certain embodiments, the aLP senses a signal from which cardiac activity associated with a ventricular chamber can be detected by the aLP itself based on feature(s) of the sensed signal. The aLP monitors the sensed signal for an intrinsic or paced ventricular activation within a ventricular event monitor window. In response to the aLP detecting an intrinsic or paced ventricular activation itself from the sensed signal within the ventricular event monitor window, the aLP resets an atrial escape interval timer that is used by the aLP to time delivery of an atrial pacing pulse if an intrinsic atrial activation is not detected within an atrial escape interval.

26 Claims, 10 Drawing Sheets

Related U.S. Application Data

(60) Provisional application No. 63/048,256, filed on Jul. 6, 2020, provisional application No. 63/033,185, filed on Jun. 1, 2020.

(51) Int. Cl.
  *A61N 1/365* (2006.01)
  *A61N 1/368* (2006.01)
  *A61N 1/372* (2006.01)
  *A61N 1/375* (2006.01)
  *A61N 1/05* (2006.01)

(52) U.S. Cl.
  CPC ......... *A61N 1/3688* (2013.01); *A61N 1/3704* (2013.01); *A61N 1/3706* (2013.01); *A61N 1/3756* (2013.01); *A61N 1/056* (2013.01)

(58) Field of Classification Search
  CPC ..... A61B 5/0004; A61B 5/1112; A61B 5/112; A61B 5/352; A61B 5/4836; A61B 5/6807; A61N 1/025; A61N 1/056; A61N 1/36507; A61N 1/3682; A61N 1/3688; A61N 1/3704; A61N 1/3706; A61N 1/37288; A61N 1/3756
  See application file for complete search history.

(56) References Cited

U.S. PATENT DOCUMENTS

| | | | |
|---|---|---|---|
| 8,781,585 | B2 | 7/2014 | Gunderson et al. |
| 8,792,971 | B2 | 7/2014 | Gunderson et al. |
| 8,923,963 | B2 | 12/2014 | Bonner et al. |
| 9,289,612 | B1 | 3/2016 | Sambelashvili et al. |
| 9,375,580 | B2 | 6/2016 | Bonner et al. |
| 9,399,140 | B2 | 7/2016 | Cho et al. |
| 9,522,280 | B2 | 12/2016 | Fishler et al. |
| 9,522,283 | B2 | 12/2016 | Bardy et al. |
| 9,694,186 | B2 | 7/2017 | Carney et al. |
| 9,808,633 | B2 * | 11/2017 | Bonner .............. A61N 1/37512 |
| 9,889,303 | B2 | 2/2018 | Brown et al. |
| 9,993,653 | B2 | 6/2018 | Bardy et al. |
| 2018/0069199 | A1 | 3/2018 | Bonner et al. |
| 2021/0370078 | A1 | 12/2021 | Min et al. |

OTHER PUBLICATIONS

Non-final Office Action dated Jul. 6, 2023, U.S. Appl. No. 17/321,014, filed May 14, 2021.

Notice of Allowance dated Dec. 22, 2023, U.S. Appl. No. 17/321,014, filed May 14, 2021.

* cited by examiner

VENTRICULAR FAR-FIELD SENSING TO GUIDE ATRIAL LEADLESS PACEMAKER AND BEYOND

PRIORITY CLAIM

The present application is a Divisional of U.S. patent application Ser. No. 17/321,014, titled VENTRICULAR FAR-FIELD SENSING TO GUIDE ATRIAL LEADLESS PACEMAKER AND BEYOND, filed on May 14, 2021, issued as U.S. Pat. No. 11,931,590, on Mar. 19, 2024, which claims priority to commonly assigned U.S. Provisional Patent Application No. 63/033,185, titled VENTRICULAR FAR-FIELD SENSING TO GUIDE ATRIAL LEADLESS PACEMAKER AND BEYOND, filed on Jun. 1, 2020, and U.S. Provisional Patent Application No. 63/048,256, titled VENTRICULAR FAR-FIELD SENSING TO GUIDE ATRIAL LEADLESS PACEMAKER AND BEYOND, filed on Jul. 6, 2020. Priority is claimed to each of the above applications, and each of the above applications is incorporated herein by reference.

FIELD OF TECHNOLOGY

Embodiments described herein generally relate to methods and systems for performing various types of pacing using leadless pacemakers, as well as various leadless pacemaker embodiments and methods for use therewith.

BACKGROUND

Some cardiac pacing systems include one or more leadless pacemakers (LPs). Such an LP of a cardiac pacing system can be used to deliver pacing pulses to a cardiac chamber within (or on) which the LP is implanted. In order to know when to deliver its pacing pulses, an LP may need to determine cardiac activity associated with another cardiac chamber. For an example, in order for an LP implanted in (or on) the right ventricular (RV) chamber to know when to deliver pacing pulses to the RV chamber, the LP may need to determine cardiac activity associate with the right atrial (RA) chamber, e.g., in order to achieve a desired atrioventricular (AV) delay. For another example, in order for an LP implanted in (or on) the RA chamber to know when to deliver pacing pulses to the RA chamber, the LP may need to determine cardiac activity associate with the RV chamber, e.g., in order to achieve a desired VA interval.

There are various different ways that an LP can determine cardiac activity associated with another cardiac chamber, in order to known when to deliver its pacing pulses. For example, an LP implanted within or on a cardiac chamber can perform implant-to-implant (i2i) communication with another LP that is implanted within or on another cardiac chamber, or the LP can sense a far-field signal indicative of cardiac activity in or on another chamber. Such i2i communication can involve one LP implanted in a cardiac chamber informing another LP implanted in or on another cardiac chamber of a paced or sensed event, so that coordinated synchronous pacing can be performed in multiple cardiac chambers. The i2i communication can be performed using RF communication techniques or conductive communication techniques. While such techniques are generally known, it would be beneficial to improve such techniques, e.g., to provide for improved pacing and/or far-field sensing.

SUMMARY

Certain embodiments of the present technology relate to methods for use with an implantable system including at least an atrial leadless pacemaker (aLP) configured to be implanted in or on an atrial chamber of a patient's heart and configured to selectively deliver a pacing pulse to the atrial chamber. Such a method can include, the aLP specifying a ventricular event monitor window, the aLP sensing a signal from which cardiac activity associated with a ventricular chamber of the patient's heart can be detected by the aLP itself based on one or more features of the sensed signal, and the aLP monitoring the sensed signal for a ventricular activation within the ventricular event monitor window. In response to the aLP detecting a ventricular activation itself from the sensed signal within the ventricular event monitor window, the method can also include the aLP resetting an atrial escape interval timer that is used by the aLP to time delivery of an atrial pacing pulse if an intrinsic atrial activation is not detected by the aLP within an atrial escape interval.

In accordance with certain embodiments, the aLP specifying a ventricular event monitor window comprises the aLP detecting or otherwise obtaining an atrial-to-ventricular interval corresponding to one or more preceding cardiac cycles, and starting the ventricular event monitor window at the detected atrial-to-ventricular interval minus a specified delta, after an intrinsic or paced atrial activation.

In accordance with certain embodiments, the aLP specifying a ventricular event monitor window comprises the aLP detecting an end of a P-wave that corresponds to an intrinsic atrial activation, and starting the ventricular event monitor window at the end of the P-wave or a specified delta after the end of the P-wave.

In accordance with certain embodiments, the implantable system also includes a ventricular leadless pacemaker (vLP) configured to be implanted in or on a ventricular chamber of the patient's heart, selectively deliver a pacing pulse to the ventricular chamber, and selectively transmit implant-to-implant (i2i) messages to the aLP. In such an embodiment the method can also include the aLP using at least one receiver of the aLP to monitor for an i2i message transmitted by the vLP, and wherein the aLP specifying a ventricular event monitor window comprises the aLP determining one of an AR-interval or a PR-interval based on an i2i message received from the vLP, and starting the ventricular event monitor window at the one of the AR-interval or the PR-interval minus a specified delta, following an intrinsic or paced atrial activation.

In accordance with certain embodiments, at least one of a start of or a duration of the ventricular event monitor window is rate adaptive by being dependent upon at least one of an atrial cycle length, a measure of temperature, or a measure of activity.

In accordance with certain embodiments, the aLP monitoring the sensed signal for a ventricular activation within a ventricular event monitor window includes at least one of the following: the aLP determining whether a magnitude associated with one or more features of the sensed signal is above a threshold level within the ventricular event monitor window; or the aLP analyzing a morphology of one or more features of the sensed signal within the ventricular event monitor window.

In accordance with certain embodiments, wherein the implantable system also includes a vLP configured to be implanted in or on a ventricular chamber of the patient's heart, selectively deliver a pacing pulse to the ventricular chamber, and selectively transmit an i2i message to the aLP, the method further comprises: the aLP using at least one receiver of the aLP to monitor for an i2i message transmitted by the vLP; and the aLP, in response to receiving an i2i message from the vLP that informs the aLP of a premature ventricular contraction (PVC) detected by the vLP, timing its delivery of an atrial pacing pulse to the atrial chamber based on the PVC.

In accordance with certain embodiments, the sensed signal, which is sensed by the aLP using electrodes thereof, comprises an electrogram (EGM) signal from which an intrinsic or paced ventricular activation can be detected by detecting a far-field R-wave or V-pulse within the ventricular event monitor window.

In accordance with certain embodiments, the sensed signal, which is sensed by the aLP using an accelerometer or pressure sensor thereof, comprises an accelerometer or pressure signal from which an intrinsic or paced ventricular activation can be detected by detecting a specific heart sound within the ventricular event monitor window, or by detecting an indication of a mechanical contraction within the ventricular event monitor window.

In accordance with certain embodiments, wherein the implantable system also includes a vLP configured to be implanted in or on a ventricular chamber of the patient's heart, selectively deliver a pacing pulse to the ventricular chamber, and receive an i2i message from the aLP, the method further comprises: the aLP monitoring for a premature atrial contraction (PAC); and the aLP, in response to detecting the PAC, transmitting an i2i message to the vLP that informs the vLP of the detected PAC, to thereby enable the vLP to time its delivery of a ventricular pacing pulse to the ventricular chamber based on the PAC.

In accordance with certain embodiments, the aLP timing its delivery of an atrial pacing pulse to the atrial chamber based on the ventricular activation detected by the aLP from the sensed signal within the ventricular event monitor window comprises: the aLP determining an AV delay as being equal to a time between a time of an intrinsic or paced atrial activation and a time of the ventricular activation detected by the aLP from the sensed signal within the ventricular event monitor window; and the aLP timing its delivery of the atrial pacing pulse to the atrial chamber a VA delay following the AV delay.

In accordance with certain embodiments, wherein the implantable system also includes a vLP configured to be implanted in or on a ventricular chamber of the patient's heart, selectively deliver a pacing pulse to the ventricular chamber, and receive an i2i message from the aLP, the method further comprises: the aLP transmitting, each cardiac cycle, an i2i message to the vLP to inform the vLP of an intrinsic or paced atrial activation, to thereby enable the vLP to time its delivery of a ventricular pacing pulse to the ventricular chamber based on the intrinsic or paced atrial activation; wherein one or more i2i messages that the aLP transmits to the vLP includes a status bit that informs the vLP whether the aLP was able to successfully detect a ventricular activation itself from the sensed signal during one or more previous cardiac cycles; and the vLP determining whether or not to transmit an i2i message to the aLP based on the status bit included in one or more i2i messages that the vLP receives from the aLP. In accordance with certain embodiments, wherein one or more i2i messages that the aLP transmits to the vLP includes a second status bit that informs the vLP whether the aLP received a valid i2i message from the vLP during one or more previous cardiac cycles, and further comprises: the vLP determining, based on the second status bit, whether to adjust at least one of an amplitude or a timing of one or more further i2i messages that the vLP transmits to the aLP.

In accordance with certain embodiments, the method further comprises the aLP disabling at least one receiver of the aLP during each ventricular event monitor window to thereby conserve energy.

Certain embodiments of the present technology are directed to an aLP configured to be implanted in or on an atrial chamber of a patient's heart, the aLP comprising at least two electrodes, and a sensing circuit electrically coupled to the at least two electrodes and configured to sense an EGM. The aLP also includes at least one of a processor or controller configured: specify a ventricular event monitor window; monitor the EGM for a ventricular activation within the ventricular event monitor window; and reset an atrial escape interval timer, in response to a ventricular activation being detected from the EGM within the ventricular event monitor window, wherein the atrial escape interval timer is used to time delivery of an atrial pacing pulse to the atrial chamber if an intrinsic atrial activation is not detected by the aLP within an atrial escape interval.

In accordance with certain embodiments, the at least one of a processor or controller is configured to start the ventricular event monitor window at a specified atrial-to-ventricular interval minus a specified delta, after a paced or sensed atrial activation; and the specified atrial-to-ventricular interval comprises one of a PV-interval, a PR-interval, an AV-interval, or an AR-interval.

In accordance with certain embodiments, the aLP further comprises a pulse generator electrically coupled to the at least two electrodes and configured to selectively generate an atrial pacing pulse; and one or more receivers configured to receive an i2i message from a vLP; wherein the at least one of a processor or controller is configured to time delivery of an atrial pacing pulse to the ventricular chamber, based on timing of a PVC, in response to the i2i message received from the vLP indicating that the PVC was detected by the vLP.

In accordance with certain embodiments, the at least one of a processor or controller of the aLP is configured to disable at least one of the one or more receivers of the aLP during each ventricular event monitor window to thereby conserve energy.

In accordance with certain embodiments, the aLP further comprises: a pulse generator electrically coupled to the at least two electrodes and configured to selectively generate conductive communication pulses for use in transmitting an i2i message to a vLP; wherein the at least one of a processor or controller is configured to cause the i2i message to be transmitted to the vLP, each cardiac cycle, to inform the vLP of an intrinsic or paced atrial activation, to thereby enable the vLP to time its delivery of a ventricular pacing pulse based on the intrinsic or paced atrial activation. Additionally, the at least one of a processor or controller is configured to include, within each i2i message, one or more status bits that at least one of informs the vLP whether the aLP was able to successfully detect an intrinsic or paced ventricular activation itself from the EGM during one or more previous cardiac cycles, or informs the vLP whether the aLP received a valid i2i message from the vLP during one or more previous cardiac cycles, thereby enabling the vLP to determine whether to adjust at least one of an amplitude or a timing of one or more further i2i messages that the vLP transmits to the aLP.

Certain embodiments of the present technology are directed to an implantable system, comprising an aLP and a vLP, wherein the aLP is configured to sense a signal from which cardiac activity associated with a ventricular chamber can be detected by the aLP itself based on one or more features of the sensed signal. The aLP is also configured to monitor the sensed signal for an intrinsic atrial activation within an atrial escape interval, and in response to an intrinsic atrial activation not being detected within the atrial escape interval, output of an atrial pacing pulse that causes a paced atrial activation. Further, the aLP is configured to monitor the sensed signal for an intrinsic or paced ventricular activation within a ventricular event monitor window that starts a specified atrial-to-ventricular interval minus a specified delta following a paced or intrinsic atrial activation. The aLP is also configured to transmit an i2i message to the vLP to inform the vLP of intrinsic or paced atrial activations. The vLP is configured to receive the i2i message transmitted by the aLP, and based thereon, time delivery of a ventricular pacing pulse based on the intrinsic or paced atrial activation.

In certain embodiments, the aLP can also be configured to include, in the i2i message, a status bit that informs the vLP whether the aLP was able to successfully detect an intrinsic or paced ventricular activation itself from the sensed signal during one or more previous cardiac cycles. Further, the vLP can be configured to determine whether or not to transmit an i2i message to the aLP based on the status bit included in one or more i2i messages that the vLP receives from the aLP.

In certain embodiments, the aLP is also configured to include, in the i2i message, a status bit that informs the vLP whether the aLP received a valid i2i message from the vLP during one or more previous cardiac cycles; and the vLP is configured to determine based on the status bit, whether to adjust at least one of an amplitude or a timing of one or more further i2i messages that the vLP transmits to the aLP.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Figure 1A:
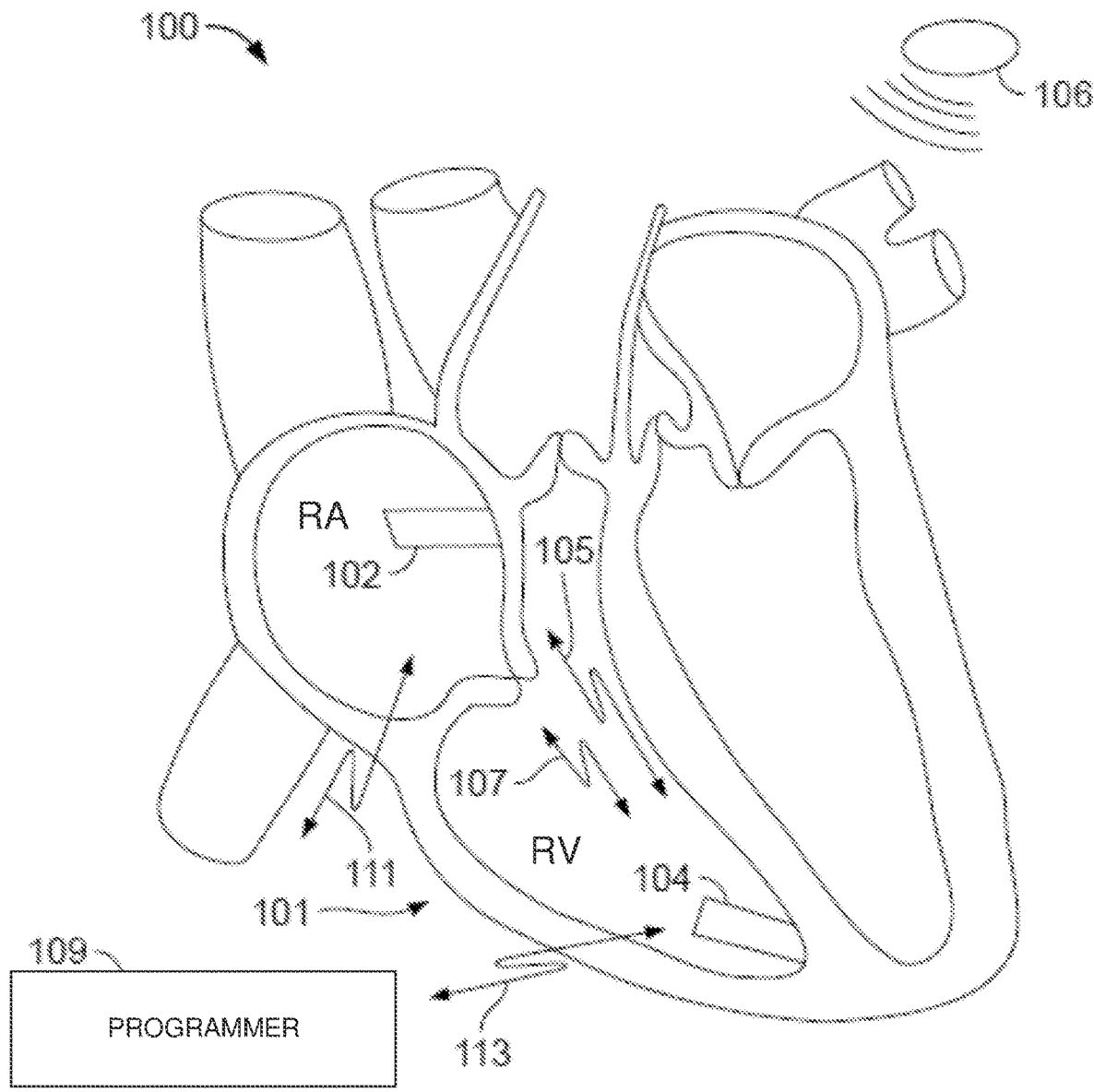
FIG. 1A illustrates a system formed in accordance with certain embodiments described herein as implanted in a heart.

Some cardiac pacing systems include one or more leadless pacemakers (LPs), as noted above, wherein such an LP can be used to deliver pacing pulses to a cardiac chamber within (or on) which the LP is implanted. In order to know when to deliver its pacing pulses, an LP may need to determine cardiac activity associated with another cardiac chamber. For an example, in order for an LP implanted in (or on) the right ventricular (RV) chamber to know when to deliver pacing pulses to the RV chamber, the LP may need to determine cardiac activity associate with the right atrial (RA) chamber, e.g., in order to achieve a desired atrio-ventricular (AV) delay. For another example, in order for an LP implanted in (or on) the RA chamber to know when to deliver pacing pulses to the RA chamber, the LP may need to determine cardiac activity associate with the RV chamber, e.g., in order to achieve a desired ventriculo-atrial (VA) interval. The LP in (or on) the patient's RA chamber can also be referred to as the aLP, and the LP in (or on) the patient's RV chamber can also be referred to as the vLP. A ventriculo-atrial (VA) interval is also known as a ventricular-atrial (VA) interval.

In certain proposed cardiac pacing systems that include vLP and aLP leadless pacemakers, the vLP and the aLP communicate with one another using implant-to-implant (i2i) conductive communication that relies on subthreshold pulses being transmitted through body tissue from one of the LPs to the other using the same electrodes of the LPs that are used for sensing and/or delivery of pacing therapy. In such a system the aLP can receive an i2i conductive communication signal from the vLP that informs the aLP of when an intrinsic or paced ventricular event occurred, thereby enabling the aLP to time its delivery of pacing pulses to the RA chamber based on information included in the i2i conductive communication signal received from the vLP. Similarly, the vLP can receive an i2i conductive communication signal from the aLP that informs the vLP of when an intrinsic or paced atrial event occurred, thereby enabling the vLP to time its delivery of pacing pulses to the RV chamber based on information including in the i2i conductive communication signal received from the aLP. A potential problem with such a cardiac pacing system is that the success of the i2i conductive communication depends on the relative orientation of the LPs, as explained below with reference to FIG. 5. Another potential problem of such a system is that generating the i2i conductive communication pulses depletes the energy stored in a battery of an LP.

When performing i2i conductive communication, the one or more pulses that are transmitted from one LP to another LP can be referred more generally as the i2i conductive communication signal. Due to the nature of electrode potential distribution, bipolar sensing of the i2i conductive communication signal (by the LP that is receiving/sensing the i2i signal) is minimal along iso-potential lines and maximum along lines orthogonal to the iso-potential lines. In other words, when the respective axes (e.g., 502 and 504 in FIG. 5 discussed below) of the two LPs (communicating with one another) are aligned with one another the sensed i2i conductive communication signal is near its maximum, and when the respective axes (e.g., 502 and 504 in FIG. 5) of the two LPs are orthogonal to one another the sensed i2i conductive communication signal is near its minimum. Indeed, both computer simulations and animal testing have shown that the sensed pulse amplitudes varied widely with different orientation angles. As an example, for a pulse amplitude of 2.5V, the sensed amplitude could vary from less than 0.5 mV to greater than 2 mV, depending on the relative orientations of the LPs.

The cardiac chamber within or on which a particular LP is implanted can be referred to as a "local chamber", while another chamber (within or on which the particular LP is not implanted) can be referred to as a "remote chamber". In accordance with certain embodiments of the present technology, one or both of an aLP or a vLP rely on far-field sensing of cardiac activity in a remote chamber to appropriately time delivery of pacing pulses to a local chamber. Such embodiments enable various different types of pacing schemes to be performed using one or more LPs. For example, in accordance with certain embodiments DDD pacing is performed using two LPs. More specifically, in accordance with certain embodiments of the present technology, an LP is implanted in (or on) a patient's RV chamber and is used to perform VDD pacing, and another LP is implanted in (or on) the patient's RA chamber and is used to perform ADD, AAI, or ADI pacing. Collectively, the two LPs can be used to perform DDD or DDI pacing or some other dual chamber pacing mode that provides synchronization between the LP1 and the LP2. Where two LPs (e.g., the LP1 and the LP2) are said to be synchronized or have synchronization provided, this means that the pacing performed by at least one of the LPs is timed relative to paced events delivered by and/or sensed events sensed by the other one of the LPs. Accordingly, two LPs can be said to be synchronized where there is VA synchrony but not AV synchrony, VA synchrony but not AV synchrony, or both VA and AV synchrony Any one of various different algorithms can be used to achieve such dual chamber pacing modes. When referring to various types of pacing schemes herein, three letters are often used to refer to the type of pacing. In other words, a three position pacemaker code is often used, with the following nomenclature followed: the first position refers to the cardiac chamber paced; the second position refers to the cardiac chamber sensed; and the third position refers to the response to a sensed event. In the first and second positions, the letter O means none, the letter A means Atrium, the letter V means Ventricle, and the letter D means Dual (i.e., A and V). In the third position the letter O means none, the letter I means Inhibited, the letter T means Triggered (aka Tracked), and the letter D means Dual (i.e., T+I). The below Table 1 summarizes this pacemaker nomenclature.

TABLE 1

| Position 1 (Chamber Paced) | Position 2 (Chamber Sensed) | Position 3 (Response to Sensed Event) |
|---|---|---|
| O = none | O = none | O = none |
| A = Atrium | A = Atrium | I = Inhibited |
| V = Ventricle | V = Ventricle | T = Triggered (aka Tracked) |
| D = Dual (A + V) | D = Dual (A + V) | D = Dual (I + T) |

Accordingly, if an LP in the patient's RV chamber performs VDD pacing, that means it paces only the RV chamber, senses both atrial and ventricular activity, and inhibits pacing of the RV if a sensed event is detected within a specified interval (the AV interval) or triggers pacing of the RV at the end of the specified interval (the AV interval) if a sensed event is not detected within that specified interval (the AV interval). For another example, if an LP in the patient's RA chamber performs AAI pacing, that means it paces only the RA chamber, senses only atrial activity, and inhibits pacing of the RA chamber if a sensed event is detected within a specified interval. Where the second position includes a "D", the LP will need to be aware of activity in its own chamber and in another chamber in or one which the LP is not implanted. Activity in another chamber can be determined from a far-field signal and/or from an i2i message received from another LP that is in or one the other chamber.

The LP in (or on) the patient's RA chamber can also be referred to as the aLP, and the LP in (or on) the patient's RV chamber can also be referred to as the vLP, as noted above. There are various different ways that an external programmer can instruct an aLP and an vLP to perform certain pacing modes that are the equivalent of pacing modes performed using conventional (i.e., non-leadless) pacemakers. For example, assume that it is desired that an aLP performs one of ADD, AAI, or ADI pacing, and the vLP performs VDD pacing, such that collectively the aLP and the vLP perform DDD or DDI pacing. The external programmer can instruct the aLP to perform a specific one of ADD, AAI, or ADI pacing, and external programmer can instruct the vLP to perform VDD pacing. Alternatively, the external programmer can instruct both of the aLP and the vLP to perform DDD or DDI pacing, in response to which the aLP will know (based on how it is programmed) to perform a specific one of ADD, AAI, or ADI pacing, and the vLP will know (based on how it is programmed) to perform VDD pacing, such that collectively the aLP and the vLP will perform DDD or DDI pacing. Other variations are also possible.

When the vLP in (or on) the RV chamber performs VDD pacing, it should know when certain cardiac activity (e.g., atrial contractions) occur in the RA chamber, so that it knows the appropriate times at which to pace the RV chamber. The vLP in (or on) the RV chamber can attempt to sense a far-field signal from which electrical cardiac activity associated with the RA chamber may be detected, and the vLP in (or on) the RV chamber can time its delivery of RV pacing pulses based on the timing of the electrical cardiac activity associated with the RA chamber detected from the far-field signal. For example, the vLP in the RV chamber may be able to detect P waves or A pulses from the electrogram (EGM) signal it senses in order to know when to deliver RV pacing pulses. However, this may not always be possible because the amplitude of P waves may be relatively low and difficult to detect from a far-field signal. The vLP in the RV chamber can alternatively or additionally use a sensor (e.g., an accelerometer or a pressure sensor) to produce a sensor signal from which the vLP in the RV chamber can detect cardiac mechanical activity associated with the RA chamber, and time its RV pacing pulses based thereon. The vLP in the RV chamber can alternatively or additionally determine the timing of atrial cardiac activity based on i2i messages received from an aLP implanted in the RA chamber.

When the aLP in (or on) the RA chamber performs ADD pacing, it should know when certain cardiac activity (e.g., ventricular contractions) occur in the RV chamber, so that it knows the appropriate times at which to pace the RA chamber. In accordance with certain embodiments, the aLP in (or on) the RA chamber senses a far-field EGM from which electrical cardiac activity associated with the RV chamber may be detected, and the aLP in (or on) the RA chamber times its delivery of RA pacing pulses based on the timing of the electrical cardiac activity associated with the RV chamber detected from the far-field signal. For example, the aLP in the RA chamber may be able to detect R waves from the far-field signal it senses in order to know when to deliver RA pacing pulses. R waves are typically much larger than P waves, and thus it is believed to be more likely that an aLP can detect R waves based on a far-field signal than a vLP can detect P waves based on a far-field signal. The aLP in the RA chamber can alternatively or additionally use a sensor (e.g., an accelerometer or a pressure sensor) to produce a sensor signal from which the aLP in the RA chamber can detect cardiac mechanical activity associated with the RV chamber, and time its RA pacing pulses based thereon. The LP in the RA chamber can alternatively or additionally determine the timing of ventricular cardiac activity based on i2i messages received from an LP implanted in the RV chamber.

In certain embodiments, the vLP in (or on) the RV chamber performs VVI pacing (e.g., using programmed VV intervals), and the aLP in (or on) the RA chamber performs ADD or ADI pacing. The ADD or ADI pacing performed by the aLP in (or on) the RA chamber can involve pacing and sensing in the RA chamber, sensing in the RV chamber (achieved by sensing a far-field signal, or producing a sensor signal from which mechanical cardiac activity in the RV chamber can be detected). Such a system would be useful for patients having sinus rhythm with heart block and intermittent atrial arrhythmia. An advantage of this system is that it could achieve dual chamber pacing and sensing with only one of LPs obtaining a far-field signal indicative of ventricular cardiac activity (which is much stronger than a far-field signal indicative of atrial cardiac activity).

In certain embodiments, the vLP in (or on) the RV chamber performs VDI pacing (e.g., using programmed VV and VA intervals), and the aLP in (or on) the RA chamber performs AAI pacing. Such a system essentially provides for DDI pacing.

Before providing addition details of the specific embodiments of the present technology mentioned above, as well as additional embodiments of the present technology, an exemplary system in which embodiments of the present technology can be used will first be described with reference to FIGS. 1A, 1B and 2. More specifically, FIGS. 1A, 1B and 2 will be used to describe an exemplary cardiac pacing system, wherein pacing and sensing operations can be performed by multiple medical devices, which may include one or more LPs, an implantable cardioverter-defibrillator (ICD), such as a subcutaneous-ICD, and/or a programmer reliably and safely coordinate pacing and/or sensing operations.

FIG. 1A illustrates a system 100 formed in accordance with certain embodiments herein as implanted in a heart 101.

The system 100 comprises two or more LPs 102 and 104 located in different chambers of the heart. LP 102 is located in the RA chamber, while LP 104 is located in the RV chamber. LPs 102 and 104 can communicate with one another to inform one another of various local physiologic activities, such as local intrinsic events, local paced events and the like. LPs 102 and 104 may be constructed in a similar manner, but operate differently based upon which chamber LP 102 or 104 is located. It is noted that the RA chamber is also known as the right atrium, and the acronym RA can be used to refer to the "right atrium" or to refer to the "right atrial" chamber. Similarly, the RV chamber is also known as the right ventricle, and the acronym RV can be used to refer to the "right ventricle" or to refer to the "right ventricular" chamber. It is also noted that the terms "cardiac chamber", "chamber of the heart", and "chamber of a patient's heart" are used interchangeably herein. The LP 102 is an example of an aLP, and the LP 104 is an example of a vLP.

In accordance with certain embodiments, the LP 102 is used to perform ADD pacing, the LP 104 is used to perform VDD pacing, and the LPs 102 and 104 are collectively used to perform DDD pacing. The ADD pacing (performed by the LP 102) involves atrial pacing, ventricular and atrial (i.e., dual) sensing, and dual (i.e., triggered and inhibited) response to a sensed event. The VDD pacing (performed by the LP 104) involves ventricular pacing, atrial and ventricular (i.e., dual) sensing, and dual (i.e., triggered and inhibited) response to a sensed event. The DDD pacing (performed collectively by the LPs 102 and 104) involves atrial and ventricular (i.e., dual) pacing, atrial and ventricular (i.e., dual) sensing, and dual (i.e., triggered and inhibited) response to a sensed event.

In some embodiments, LPs 102 and 104 communicate with one another, with an ICD 106, and with an external device (e.g., programmer) 109 through wireless transceivers, communication coils and/or antenna, and/or by conductive communication through the same electrodes as (or one or more different electrodes than) used for sensing and/or delivery of pacing therapy. When conductive communication is performed using electrodes, the system 100 may omit an antenna or telemetry coil in one or more of LPs 102 and 104.

In some embodiments, one or more LPs 102 and 104 can be co-implanted with the ICD 106. Each LP 102, 104 uses two or more electrodes located within, on, or within a few centimeters of the housing of the LP, for pacing and sensing at the cardiac chamber, for bidirectional communication with one another, with the programmer 109 (or some other external device), and the ICD 106.

In FIG. 1A, the two LPs 102 and 104 are shown as being implanted endocardially, i.e., within respective cardiac chambers. In other words, in FIG. 1A each of the LPs 102 and 104 is shown as being implanted in a respective cardiac chamber, i.e., the LP 102 is shown as being implanted in the RA chamber, and the LP 104 is shown as being implanted in the RV chamber. Alternatively, one or both of the LPs 102 and 104 can be implanted epicardially (on the external heart surface) by affixing to the exterior surface of the heart. For example, it would also be possible for the LP 102 to be affixed to an exterior surface of the RA chamber, in which case the LP 102 can be said to be implanted on (rather than in) the RA chamber. Similarly, it would also be possible for the LP 104 to be affixed to an exterior of the RV chamber, in which case the LP 104 can be said to be implanted on (rather than in) the RV chamber. More generally, an LP can either be implanted in or on the cardiac chamber that the LP is being used to pace. It is noted that the terms "implanted in," "implanted within," "located in," and "located within" are used interchangeably herein when referring to where a particular LP is implanted. Further, it is noted that the terms "located on" and "implanted on" are used interchangeably herein when referring to where a particular LP is implanted. As noted above, the cardiac chamber within or on which a particular LP is implanted can be referred to as a "local chamber", while another chamber (within or on which the particular LP is not implanted) can be referred to as a "remote chamber". The LP 102 is an example of an aLP, and the LP 104 is an example of a vLP.

In accordance with certain embodiments, methods are provided for coordinating operation between LPs located in or on different cardiac chambers of the heart. Some such methods can configure a local LP to receive communications from a remote LP through conductive communication. Some such methods rely on a local LP sensing a far-field signal and/or a sensor signal to itself monitor cardiac activity associated with a remote cardiac chamber.

Figure 1B:
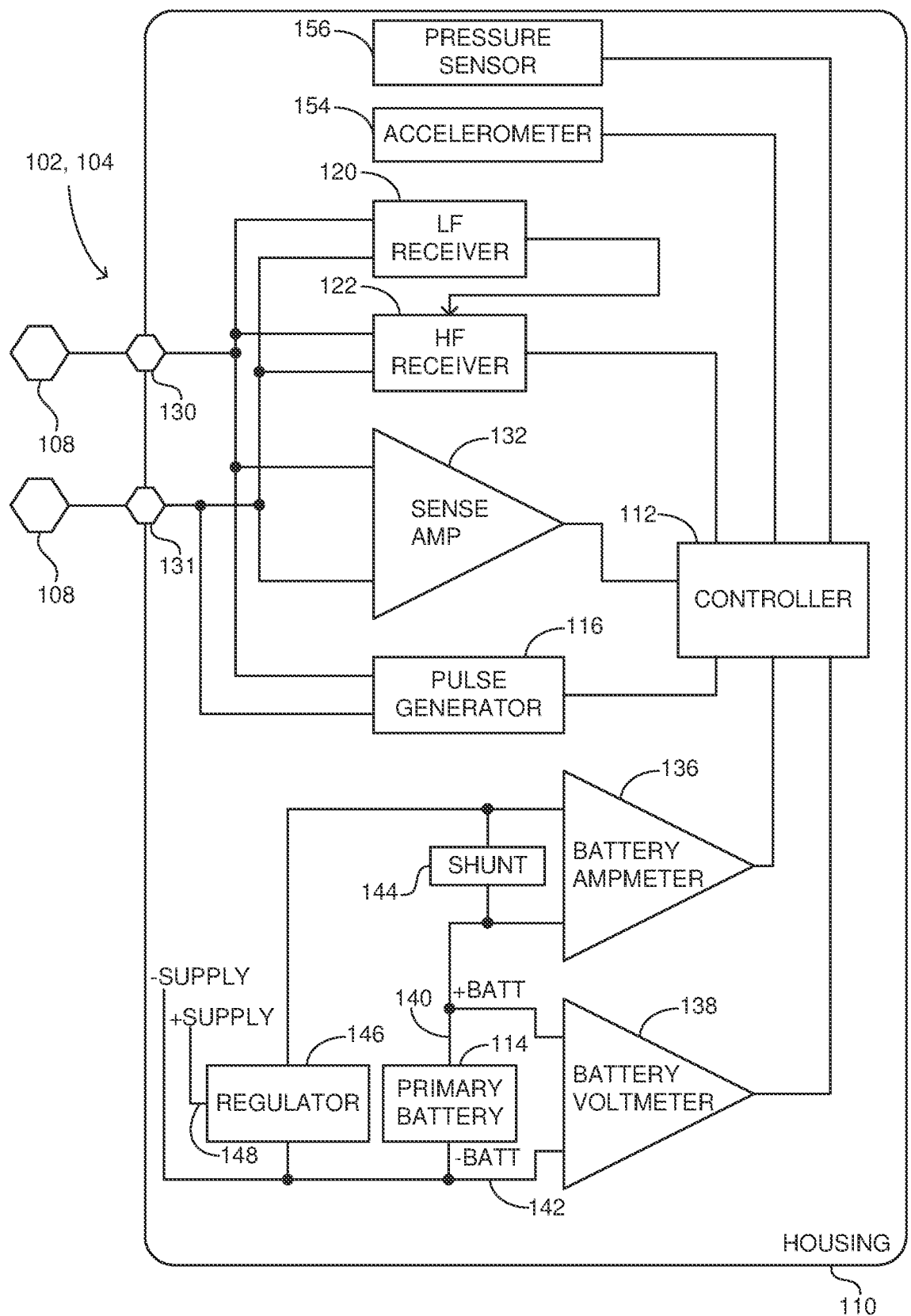
FIG. 1B is a block diagram of an exemplary leadless pacemaker (LP) in accordance with certain embodiments herein.

Referring to FIG. 1B, a block diagram shows exemplary electronics within LPs 102 and 104. LP 102, 104 includes first and second receivers 120 and 122 that collectively define separate first and second communication channels 105 and 107 (FIG. 1A), (among other things) between LPs 102 and 104. Although first and second receivers 120 and 122 are depicted, in other embodiments, LP 102, 104 may only include first receiver 120, or may include additional receivers other than first and second receivers 120 and 122. As will be described in additional detail below, the pulse generator 116 can function as a transmitter that transmits implant-to-implant (i2i) communication signals using the electrodes 108. Usage of the electrodes 108 for communication enables the one or more LPs 102 and 104 to perform antenna-less and telemetry coil-less communication.

In accordance with certain embodiments, when one of the LPs 102 and 104 senses an intrinsic event or delivers a paced event, the corresponding LP 102, 104 transmits an implant event message to the other LP 102, 104. For example, when an atrial LP 102 senses/paces an atrial event, the atrial LP 102 transmits an implant event message including an event marker indicative of a nature of the event (e.g., intrinsic/sensed atrial event, paced atrial event). When a ventricular LP 104 senses/paces a ventricular event, the ventricular LP 104 transmits an implant event message including an event marker indicative of a nature of the event (e.g., intrinsic/sensed ventricular event, paced ventricular event). In certain embodiments, LP 102, 104 transmits an implant event message to the other LP 102, 104 preceding the actual pace pulse so that the remote LP can blank its sense inputs in anticipation of that remote pace pulse (to prevent inappropriate crosstalk sensing).

Still referring to FIG. 1B, each LP 102, 104 is shown as including a controller 112 and a pulse generator 116. The controller 112 can include, e.g., a microprocessor (or equivalent control circuitry), RAM and/or ROM memory, logic and timing circuitry, state machine circuitry, and I/O circuitry, but is not limited thereto. The controller 112 can further include, e.g., timing control circuitry to control the timing of the stimulation pulses (e.g., pacing rate, atrio-ventricular (AV) delay, atrial interconduction (A-A) delay, or ventricular interconduction (V-V) delay, etc.). Such timing control circuitry may also be used for the timing of refractory periods, blanking intervals, noise detection windows, evoked response windows, alert intervals, marker channel timing, and so on. The controller 112 can further include other dedicated circuitry and/or firmware/software components that assist in monitoring various conditions of the patient's heart and managing pacing therapies. The controller 112 and the pulse generator 116 may be configured to transmit event messages, via the electrodes 108, in a manner that does not inadvertently capture the heart in the chamber where LP 102, 104 is located, such as when the associated chamber is not in a refractory state. In addition, a LP 102, 104 that receives an event message may enter an "event refractory" state (or event blanking state) following receipt of the event message. The event refractory/blanking state may be set to extend for a determined period of time after receipt of an event message in order to avoid the receiving LP 102, 104 from inadvertently sensing another signal as an event message that might otherwise cause retriggering. For example, the receiving LP 102, 104 may detect a measurement pulse from another LP 102, 104 or programmer 109. The controller 112 in FIG. 1B (and the programmable microcontroller 820 in FIG. 8 described below) are examples of a controller and/or processor that can be used to perform the methods summarized below, e.g., with reference to FIGS. 6A, and 6B as well as other FIGS.

In accordance with certain embodiments herein, the programmer 109 may communicate over a programmer-to-LP channel, with LP 102, 104 utilizing the same communication scheme. The external programmer 109 may listen to the event message transmitted between LP 102, 104 and synchronize programmer to implant communication such that programmer 109 does not transmit communication signals 113 until after an implant to implant messaging sequence is completed. Alternatively, the external programmer 109 may wait for a directed communication message transmitted to the external programmer 109 from LP 102 or 104 that indicates to the external programmer 109 that that the LP is ready to trade communication signals 113 with the external programmer 109. An LP 102, 104 can also communicate with other types of external devices besides the external programmer 109, such as, but not limited to, an external monitor.

In accordance with certain embodiments, LP 102, 104 may combine transmit operations with therapy. The transmit event marker may be configured to have similar characteristics in amplitude and pulse-width to a pacing pulse and LP 102, 104 may use the energy in the event messages to help capture the heart. For example, a pacing pulse may normally be delivered with pacing parameters of 2.5V amplitude, 500 ohm impedance, 60 bpm pacing rate, 0.4 ms pulse-width. The foregoing pacing parameters correspond to a current draw of about 1.9 µA. The same LP 102, 104 may implement an event message utilizing event signaling parameters for amplitude, pulse-width, pulse rate, etc. that correspond to a current draw of approximately 0.5 µA for transmit.

LP 102, 104 may combine the event message transmissions with pacing pulses. For example, LP 102, 104 may use a 50 µs wakeup transmit pulse having an amplitude of 2.5V which would draw 250 nC (nano Coulombs) for an electrode load of 500 ohm. The pulses of the transmit event message may be followed by an event message encoded with a sequence of short duration pulses (for example 16, 2 us on/off bits) which would draw an additional 80 nC. The event message pulse would then be followed by the remaining pulse-width needed to reach an equivalent charge of a nominal 0.4 ms pace pulse. In this case, the current necessary to transmit the marker is essentially free as it was used to achieve the necessary pace capture anyhow. With this method, the savings in transmit current could be budgeted for the receiver or would allow for additional longevity.

When LP 102 or 104 senses an intrinsic event, it can send a qualitatively similar event pulse sequence (but indicative of a sensed event) without adding the pace pulse remainder. As LP 102, 104 longevity calculations are designed based on the assumption that LP 102, 104 will deliver pacing therapy 100% of the time, transmitting an intrinsic event marker to another LP 102, 104 will not impact the nominal calculated LP longevity.

In some embodiments, the individual LP 102 can comprise a hermetic housing 110 configured for placement on or attachment to the inside or outside of a cardiac chamber and at least two leadless electrodes 108 proximal to the housing 110 and configured for bidirectional communication with at least one other device 106 within or outside the body. As will be described in additional detail below, with reference to FIGS. 9A and 9B, in certain embodiments an individual LP includes two hermetic housings, one of which includes electronic circuitry, and the other of which includes a battery.

Referring to FIG. 1B, the LP 102 (or 104) is shown as including an accelerometer 154 which can be hermetically contained within the housing 110. The accelerometer 154 can be any one of various different types of known accelerometers, or can be a future developed accelerometer. For one example, the accelerometer 154 can be or include, e.g., a MEMS (micro-electromechanical system) multi-axis accelerometer of the type exploiting capacitive or optical cantilever beam techniques, or a piezoelectric accelerometer that employs the piezoelectric effect of certain materials to measure dynamic changes in mechanical variables. Where the accelerometer is a multi-axis accelerometer it can include two or three sensors aligned along orthogonal axes. Exemplary multi-axis accelerometers (also referred to as multi-dimensional accelerometers) that can be used are described in U.S. Pat. No. 6,658,292 (Kroll et al.) and U.S. Pat. No. 6,466,821 (Pianca et al.), each of which is incorporated herein by reference. For another example, a commercially available micro-electromechanical system (MEMS) accelerometer marketed as the ADXL345 by Analog Devices, Inc. (headquartered in Norwood, Massachusetts) is a three-axis accelerometer and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL345 includes a micro-machined accelerometer co-packaged with a signal processing IC.

Another commercially available MEMS accelerometer is the ADXL327 by Analog Devices, Inc., which is a small, thin, low power, complete three axis accelerometer with signal conditioned voltage outputs. In the ADXL327, the mechanical sensor and signal conditioning IC are packaged together. A further commercially available MEMS accelerometer that can be used is the LIS3DH three-axis accelerometer by STMicroelectronics (headquartered in Geneva, Switzerland). Additional and/or alternative types of accelerometers may also be used. For example, it is also within the scope of the present technology for the accelerometer 154 to be a beam-type of accelerometer, an example of which is described in U.S. Pat. No. 6,252,335 (Nilsson et al.), which is incorporated herein by reference.

The accelerometer 154 can be, e.g., a one-dimensional (1D) accelerometer (also known as a one-axis accelerometer), a two-dimensional (2D) accelerometer (also known as a two-axis accelerometer), or a three-dimensional (3D) accelerometer (also known as a three-axis accelerometer). A 1D accelerometer measures acceleration along one axis, e.g., the z-axis. A 2D accelerometer measures acceleration along two axes that are orthogonal to one another, e.g., the z-axis, and the x- or y-axis. A 3D accelerometer measures acceleration along three axes that are orthogonal to one another, e.g., the z-axis, the x-axis, and the y-axis. Each measure of acceleration (i.e., rate of change of velocity) can actually be a measure of proper acceleration, which is the rate of change of velocity of a body in its own instantaneous rest frame. For example, an accelerometer at rest on the surface of the Earth will measure an acceleration due to Earth's gravity, straight upwards (by definition) of g=9.81 m/s^2.

Where an LP (e.g., LP 102 or 104) includes an accelerometer within a housing of the LP or attached thereto, the accelerometer can be used to measure the acceleration of the LP along one or more axes, which measurement(s) can be used to determine the orientation of the LP. Accordingly, because the output(s) of the accelerometer can be used to determine the orientation of the LP, it can be said that the output(s) of the accelerometer (e.g., 154) are indicative of an orientation of the LP (e.g., LP 102 or 104). More specifically, in accordance with certain embodiments, the controller 112 of an LP 102 (or 104) receives one or more outputs output(s) of the accelerometer 154, which is/are indicative of an orientation of the LP 102 (or 104). In such embodiments, the controller 112 can determine, based on the output(s) received from the accelerometer 154, an actual orientation of the LP 102 (or 104). Each output of the accelerometer 154 can comprise a respective signal.

One or more signals produced and output by the accelerometer 154 may be analyzed with respect to frequency content, energy, duration, amplitude and/or other characteristics. Such signals may or may not be amplified and/or filtered prior to being analyzed. For example, filtering may be performed using lowpass, highpass and/or bandpass filters. The signals output by the accelerometer 154 can be analog signals, which can be analyzed in the analog domain, or can be converted to digital signals (by an analog-to-digital converter) and analyzed in the digital domain. Alternatively, the signals output by the accelerometer 154 can already be in the digital domain.

The one or more signals output by the accelerometer 154 can be analyzed by the controller 112 and/or other circuitry. In certain embodiments, the accelerometer 154 is packaged along with an integrated circuit (IC) that is designed to analyze the signal(s) it generates. In such embodiments, one or more outputs of the packaged sensor/IC can be an indication of acceleration along one or more axes. In other embodiments, the accelerometer 154 can be packaged along with an IC that performs signal conditioning (e.g., amplification and/or filtering), performs analog-to-digital conversions, and stores digital data (indicative of the sensor output) in memory (e.g., RAM, which may or may not be within the same package). In such embodiments, the controller 112 or other circuitry can read the digital data from the memory and analyze the digital data. Other variations are also possible, and within the scope of embodiments of the present technology. In accordance with certain embodiments of the present technology, described in additional detail below, a sensor signal produced by the accelerometer 154 of an LP implanted in or on a cardiac chamber can be used to detect mechanical cardiac activity associated with another cardiac chamber.

FIG. 1B depicts a single LP 102 (or 104) and shows the LP's functional elements substantially enclosed in a hermetic housing 110. The LP 102 (or 104) has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, receivers 120, 122 for receiving information from at least one other device via the electrodes 108, and the pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

In FIG. 1B, all of the components shown within the housing 110, besides the battery 114, can be referred generally as electrical circuitry or electronics of the LP 102, 104. In FIG. 1B the battery 114 and the electronics are shown as being within the same housing 110. In certain embodiments of the present technology, described below with reference to FIGS. 9A and 9B, the battery 114 and the electronics are included within separate respective electrically conductive housings (e.g., 912 and 922 in FIG. 9A) that are electrically isolated from one another.

The electrodes 108 can be configured to communicate bidirectionally among the multiple LPs and/or the implanted ICD 106 to coordinate pacing pulse delivery and optionally other therapeutic or diagnostic features using messages that identify an event at an individual LP originating the message and an LP receiving the message react as directed by the message depending on the origin of the message. An LP 102, 104 that receives the event message reacts as directed by the event message depending on the message origin or location. In some embodiments or conditions, the two or more leadless electrodes 108 can be configured to communicate bidirectionally among the one or more LPs 102, 104 and/or the ICD 106 and transmit data including designated codes for events detected or created by an individual LP. Individual LPs can be configured to issue a unique code corresponding to an event type and a location of the sending pacemaker. While the LP 102, 104 shown in FIG. 1B is shown as including only two electrodes 108, in alternative embodiments discussed below, an LP can include more than two electrodes.

In some embodiments, an individual LP 102, 104 can be configured to deliver a pacing pulse with an event message encoded therein, with a code assigned according to pacemaker location and configured to transmit a message to one or more other LPs via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 104 may receive and relay an event message from LP 102 to the programmer. Similarly, information communicated on the outgoing channel can also include a message to another LP, or to the ICD, that the sending leadless cardiac pacemaker has sensed a heartbeat or has delivered a pacing pulse at the location of the sending pacemaker.

Referring again to FIGS. 1A, the cardiac pacing system 100 may comprise an implantable cardioverter-defibrillator (ICD) 106 in addition to LPs 102, 104 configured for implantation in electrical contact with a cardiac chamber and for performing cardiac rhythm management functions in combination with the implantable ICD 106. The implantable ICD 106 and the one or more LPs 102, 104 can be configured for leadless intercommunication by information conduction through body tissue and/or wireless transmission between transmitters and receivers in accordance with the discussed herein.

As shown in the illustrative embodiments, an LP 102, 104 can comprise two or more leadless electrodes 108 configured for delivering cardiac pacing pulses, sensing evoked and/or natural cardiac electrical signals, and bidirectionally communicating with the co-implanted ICD 106.

LPs 102, 104 can be configured for operation in a particular location and a particular functionality at manufacture and/or at programming by an external programmer 109. Bidirectional communication among the multiple leadless cardiac pacemakers can be arranged to communicate notification of a sensed heartbeat or delivered pacing pulse event and encoding type and location of the event to another implanted pacemaker or pacemakers. LP 102, 104 receiving the communication decode the information and respond depending on location of the receiving pacemaker and predetermined system functionality.

In some embodiments, the LPs 102 and 104 are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, or one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking and refractory periods, etc. Accordingly, each LP preferably knows an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or VVI), and for the IPG to utilize the proper set of settings and algorithms (e.g., V-AutoCapture vs. ACapConfirm, sensing sensitivities, etc.).

Also shown in FIG. 1B, the primary battery 114 has positive pole 140 and negative pole 142. Current from the positive pole 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the controller 112 with an indication of battery current drain and indirectly of device health. The illustrative power supply can be a primary battery 114.

In various embodiments, LP 102, 104 can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one LP 102, 104 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

In certain embodiments, the electrodes of an LP 102, 104 can be used to sense an electrogram (EGM) from which atrial and/or ventricular activity can be detected, e.g., by detecting R waves and/or P waves. Accordingly, the sensed EGM can be used by an LP to time its delivery of pacing pulses. Where an EGM sensed by an LP is indicative of electrical cardiac activity associated with the same cardiac chamber within or on which an LP is implanted, the EGM can be referred to as a near-field signal. Where an EGM sensed by an LP is indicative of electrical cardiac activity associate with another cardiac chamber of the heart (other than the cardiac chamber within or on which the LP is implanted), the EGM can be referred to as a far-field signal. An EGM can also be used by an LP 102, 104 to time when i2i communication pulses should be generated and transmitted, since the orientation of the LPs 102, 104 relative to one another can change throughout each cardiac cycle.

Referring briefly back to FIG. 1B, only one sense amplifier 132 was shown within the LP illustrated therein. In accordance with certain embodiments, an LP includes multiple sense amplifiers, e.g., one or more for sensing near-field signals, one or more for sensing far-field signals, and one or more for sensing i2i signals. Each such sense amplifier can include one or more filters within the amplifier, upstream from the amplifier and/or downstream from the amplifier. Such filter(s) can be used to filter out motion artifacts, DC drift, and/or the like.

In FIG. 1B only one pulse generator 116 was shown within the LP illustrated therein. In accordance with certain embodiments, an LP (e.g., 102, 104) includes multiple pulse generators, e.g., one for generating pacing signals, and one or more for generating i2i signals. Further, while the LP in FIG. 1B and other FIGS. was shown as including only two electrodes 108, it is possible that an LP can include three or more electrodes, in which case switch circuitry can be located between the electrodes and the sense amplifier(s) and pulse generator(s), to enable a controller (e.g., 112) to control which electrodes are used to sense a near-field signal, which electrodes are used to sense a far-field signal, which electrodes are used for pacing, and to control which electrodes are used for i2i communications.

Figure 2:
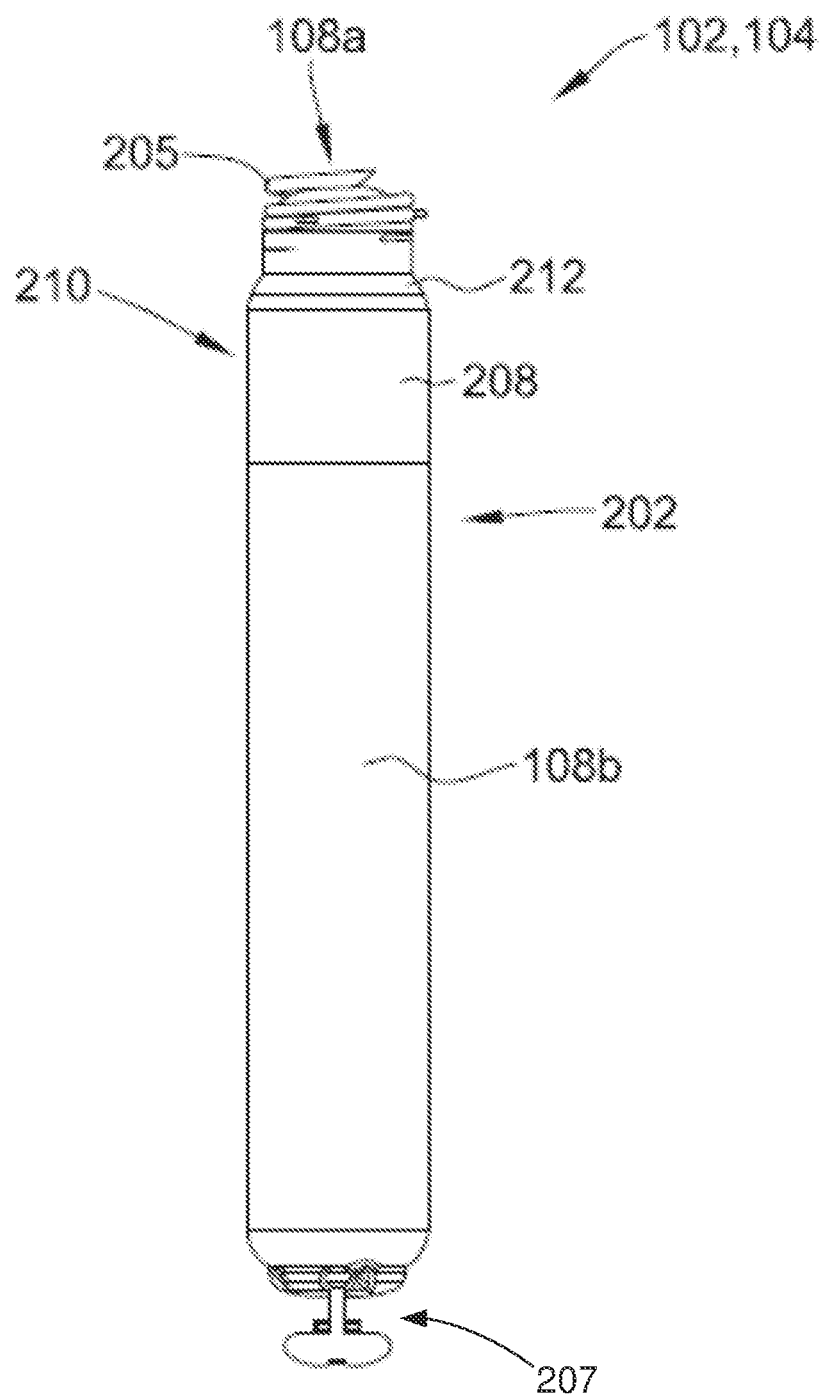
FIG. 2 illustrates an LP in accordance with certain embodiments herein.

FIG. 2 shows an LP 102, 104. The LP can include a hermetic housing 202 (e.g., the housing 110 in FIG. 1) with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue. The electrodes 108a and 108b are examples of the electrodes 108 shown in and discussed above with reference to FIG. 1B. One of the electrodes 108 (e.g., 108a) can function as a cathode type electrode and another one of the electrodes 108 (e.g., 108b) can function as an anode type electrode, or vice versa, when the electrodes are used for delivering stimulation. The electrode 108a is an example of a tip electrode, and the electrode 108b is an example or a ring electrode. The electrodes 108a and 108b can be referred to collectively as the electrodes 108, or individually as the electrode 108. While the LP 102, 104 shown in FIG. 2 is shown as including only two electrodes 108, in alternative embodiments discussed below, an LP can include more than two electrodes. The LP 102, 104 shown in FIG. 2 is also shown as including a retrieval feature 207, which can include a "button" or circular grasping feature that is configured to dock within a docking cap or a retrieval catheter that can be used to remove the LP 102, 104 when it needs to be removed and/or replaced. Alternative form factors for the retrieval feature are also possible.

Where an LP includes more than two electrodes, a first subset of the electrodes can be used for delivering pacing pulses, a second subset of the electrodes can be used for sensing a near-field signal, a third subset of the electrodes can be used for sensing a far-field signal, and a fourth subset of the electrodes can be used for transmitting and receiving i2i messages. One or more of the first, second, third, and forth subsets of electrodes can be the same, or they can all differ from one another. As used herein, the term near-field signal refers to a signal that originates in a local chamber (i.e., the same chamber) within which or on which corresponding sense electrodes (and the LP including the sense electrodes) are located. Conversely, the term far-field signal refers to a signal that originates in a chamber other than the local chamber within which or on which corresponding sense electrodes (and the LP including the sense electrodes) are located.

The housing 202 can also include an electronics compartment 210 within the housing that contains the electronic components necessary for operation of the pacemaker, including, e.g., a pulse generator, receiver, and a processor for operation. The hermetic housing 202 can be adapted to be implanted on or in a human heart, and can be cylindrically shaped, rectangular, spherical, or any other appropriate shapes, for example.

The housing 202 can comprise a conductive, biocompatible, inert, and anodically safe material such as titanium, 316L stainless steel, or other similar materials. The housing 202 can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 2, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 2, the pacemaker can further include a header assembly 212 to isolate electrodes 108a and 108b. The header assembly 212 can be made from PEEK, tecothane or another biocompatible plastic, and can contain a ceramic to metal feedthrough, a glass to metal feedthrough, or other appropriate feedthrough insulator as known in the art.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 2, electrode 108a can be a pace/sense electrode and electrode 108b can be a return electrode. The electrode 108b can be a portion of the conductive housing 202 that does not include an insulator 208. As noted above, and described in additional detail below, an LP can include more than two electrodes, and may use different combinations of the electrodes for sensing a near-field signal, sensing a far-field signal, delivering pacing pulses, and sending and receiving i2i messages. When the electrode 108a is used as a pace electrode it can also be referred to as the cathode.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 2) into contact with stimulable tissue. Electrode 108b can serve as an indifferent electrode (also referred to as the anode) for sensing and pacing. The fixation mechanism may be coated partially or in full for electrical insulation, and a steroid-eluting matrix may be included on or near the device to minimize fibrotic reaction, as is known in conventional pacing electrode-leads.

Implant-to-Implant (i2i) Event Messaging

LPs 102 and 104 can utilize implant-to-implant (i2i) communication through event messages to coordinate operation with one another in various manners. The terms i2i communication, i2i event messages, and i2i even markers are used interchangeably herein to refer to event related messages and IMD/IMD operation related messages transmitted from an implanted device and directed to another implanted device (although external devices, e.g., a programmer, may also receive i2i event messages). In certain embodiments, LP 102 and LP 104 operate as two independent leadless pacers maintaining beat-to-beat dual-chamber functionality via a "Master/Slave" operational configuration. For descriptive purposes, the ventricular LP 104 shall be referred to as "vLP" and the atrial LP 102 shall be referred to as "aLP". LP 102, 104 that is designated as the master device (e.g. vLP) may implement all or most dual-chamber diagnostic and therapy determination algorithms. For purposes of the following illustration, it is assumed that the vLP is a "master" device, while the aLP is a "slave" device. Alternatively, the aLP may be designated as the master device, while the vLP may be designated as the slave device. The master device orchestrates most or all decision-making and timing determinations (including, for example, rate-response changes).

In accordance with certain embodiments, methods are provided for coordinating operation between first and second leadless pacemakers (LPs) configured to be implanted entirely within (or alternatively on) first and second chambers of the heart. A method transmits an event marker through conductive communication through electrodes located along a housing of the first LP, the event marker indicative of one of a local paced or sensed event. The method detects, over a sensing channel, the event marker at the second LP. The method identifies the event marker at the second LP based on a predetermined pattern configured to indicate that an event of interest has occurred in a remote chamber. In response to the identifying operation, the method initiates a related action in the second LP.

Figure 3:
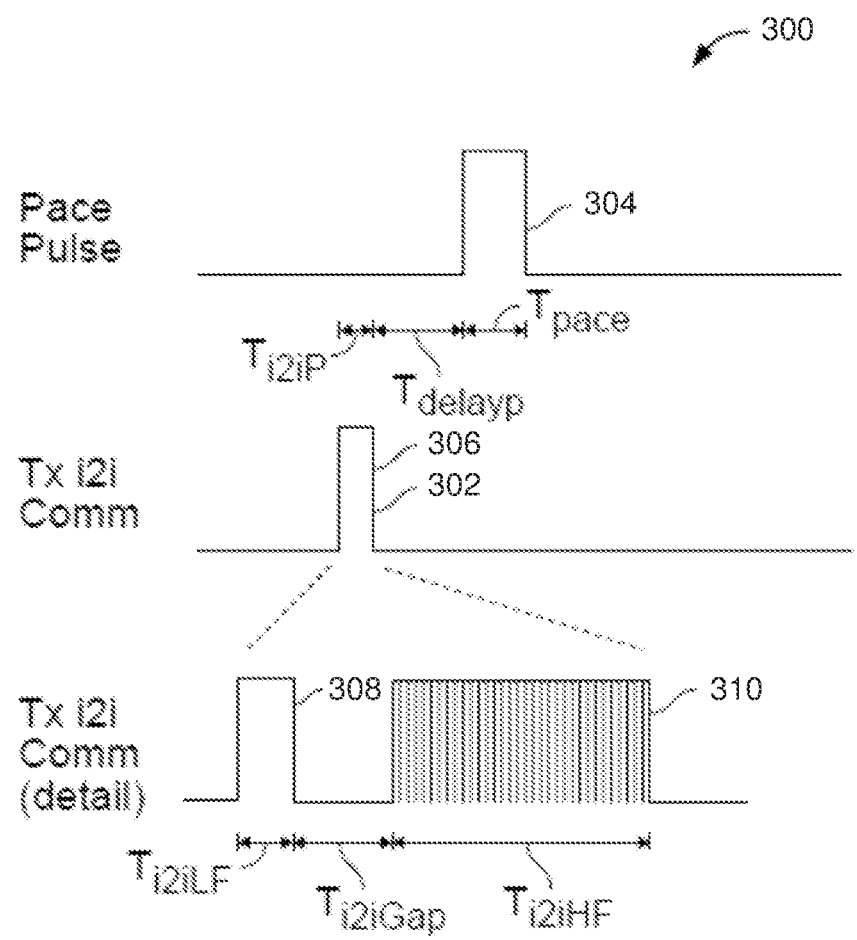
FIG. 3 is a timing diagram demonstrating one embodiment of implant to implant (i2i) communication for a paced event.

FIG. 3 is a timing diagram 300 demonstrating one example of an i2i communication for a paced event. The i2i communication may be transmitted, for example, from LP 102 to LP 104. As shown in FIG. 3, in this embodiment, an i2i transmission 302 is sent prior to delivery of a pace pulse 304 by the transmitting LP (e.g., LP 102). This enables the receiving LP (e.g., LP 104) to prepare for the remote delivery of the pace pulse. The i2i transmission 302 includes an envelope 306 that may include one or more individual pulses. For example, in this embodiment, envelope 306 includes a low frequency pulse 308 followed by a high frequency pulse train 310. Low frequency pulse 308 lasts for a period $T_{i2iLF}$, and high frequency pulse train 310 lasts for a period $T_{i2iHF}$. The end of low frequency pulse 308 and the beginning of high frequency pulse train 310 are separated by a gap period, $T_{i2iGap}$.

As shown in FIG. 3, the i2i transmission 302 lasts for a period Ti2iP, and pace pulse 304 lasts for a period Tpace. The end of i2i transmission 302 and the beginning of pace pulse 304 are separated by a delay period, TdelayP. The delay period may be, for example, between approximately 0.0 and 10.0 milliseconds (ms), particularly between approximately 0.1 ms and 2.0 ms, and more particularly approximately 1.0 ms. The term approximately, as used herein, means +/−10% of a specified value.

Figure 4:
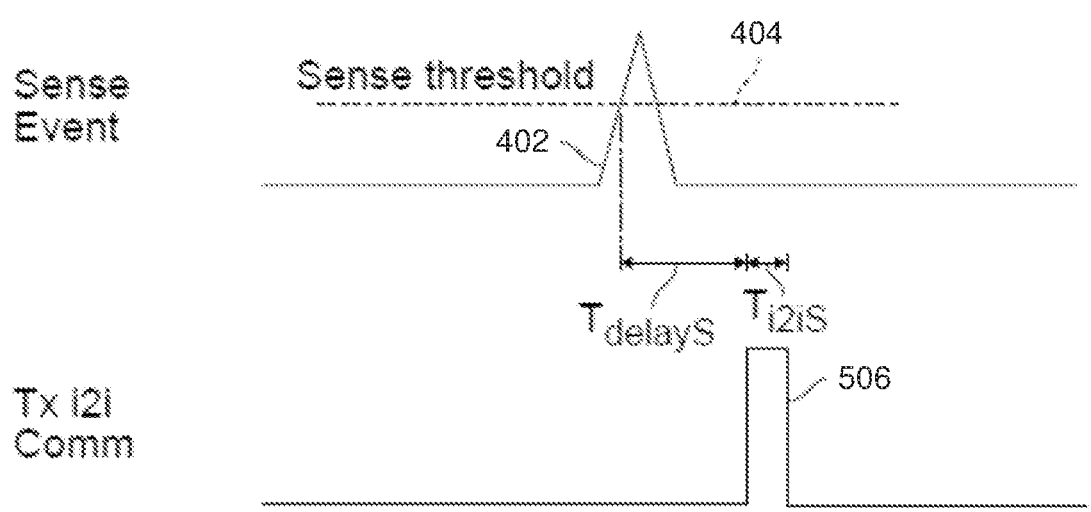
FIG. 4 is a timing diagram demonstrating one embodiment of i2i communication for a sensed event.

FIG. 4 is a timing diagram 400 demonstrating one example of an i2i communication for a sensed event. The i2i communication may be transmitted, for example, from LP 102 to LP 104. As shown in FIG. 4, in this embodiment, the transmitting LP (e.g., LP 102) detects the sensed event when a sensed intrinsic activation 402 crosses a sense threshold 404. A predetermined delay period, $T_{delayS}$, after the detection, the transmitting LP transmits an i2i transmission 406 that lasts a predetermined period $T_{i2iS}$. The delay period may be, for example, between approximately 0.0 and 10.0 milliseconds (ms), particularly between approximately 0.1 ms and 2.0 ms, and more particularly approximately 1.0 ms.

As with i2i transmission 302, i2i transmission 406 may include an envelope that may include one or more individual pulses. For example, similar to envelope 406, the envelope of i2i transmission 406 may include a low frequency pulse followed by a high frequency pulse train.

Optionally, wherein the first LP is located in an atrium and the second LP is located in a ventricle, the first LP produces an AS/AP event marker to indicate that an atrial sensed (AS) event or atrial paced (AP) event has occurred or will occur in the immediate future. For example, the AS and AP event markers may be transmitted following the corresponding AS or AP event. Alternatively, the first LP may transmit the AP event marker slightly prior to delivering an atrial pacing pulse. Alternatively, wherein the first LP is located in an atrium and the second LP is located in a ventricle, the second LP initiates an atrioventricular (AV) interval after receiving an AS or AP event marker from the first LP; and initiates a post atrial ventricular blanking (PAVB) interval after receiving an AP event marker from the first LP.

Optionally, the first and second LPs may operate in a "pure" master/slave relation, where the master LP delivers "command" markers in addition to or in place of "event" markers. A command marker directs the slave LP to perform an action such as to deliver a pacing pulse and the like. For example, when a slave LP is located in an atrium and a master LP is located in a ventricle, in a pure master/slave relation, the slave LP delivers an immediate pacing pulse to the atrium when receiving an AP command marker from the master LP.

In accordance with some embodiments, communication and synchronization between the aLP and vLP is implemented via conducted communication of markers/commands in the event messages (per i2i communication protocol). As explained above, conducted communication represents event messages transmitted from the sensing/pacing electrodes at frequencies outside the RF or Wi-Fi frequency range. Alternatively, the event messages may be conveyed over communication channels operating in the RF or Wi-Fi frequency range. The figures and corresponding description below illustrate non-limiting examples of markers that may be transmitted in event messages. The figures and corresponding description below also include the description of the markers and examples of results that occur in the LP that receives the event message. Table 2 represents exemplary event markers sent from the aLP to the vLP, while Table 3 represents exemplary event markers sent from the vLP to the aLP. In the master/slave configuration, AS event markers are sent from the aLP each time that an atrial event is sensed outside of the post ventricular atrial blanking (PVAB) interval or some other alternatively-defined atrial blanking period. The AP event markers are sent from the aLP each time that the aLP delivers a pacing pulse in the atrium. The aLP may restrict transmission of AS markers, whereby the aLP transmits AS event markers when atrial events are sensed both outside of the PVAB interval and outside the post ventricular atrial refractory period (PVARP) or some other alternatively-defined atrial refractory period. Alternatively, the aLP may not restrict transmission of AS event markers based on the PVARP, but instead transmit the AS event marker every time an atrial event is sensed.

TABLE 2

"A2V" Markers/Commands (i.e., from aLP to vLP)

| Marker | Description | Result in vLP |
|---|---|---|
| AS | Notification of a sensed event in atrium (if not in PVAB or PVARP) | Initiate AV interval (if not in PVA or PVARP) |
| AP | Notification of a paced event in atrium | Initiate PAVB Initiate AV interval (if not in PVARP) |

As shown in Table 2, when an aLP transmits an event message that includes an AS event marker (indicating that the aLP sensed an intrinsic atrial event), the vLP initiates an AV interval timer. If the aLP transmits an AS event marker for all sensed events, then the vLP would preferably first determine that a PVAB or PVARP interval is not active before initiating an AV interval timer. If however the aLP transmits an AS event marker only when an intrinsic signal is sensed outside of a PVAB or PVARP interval, then the vLP could initiate the AV interval timer upon receiving an AS event marker without first checking the PVAB or PVARP status. When the aLP transmits an AP event marker (indicating that the aLP delivered or is about to deliver a pace pulse to the atrium), the vLP initiates a PVAB timer and an AV interval time, provided that a PVARP interval is not active. The vLP may also blank its sense amplifiers to prevent possible crosstalk sensing of the remote pace pulse delivered by the aLP.

TABLE 3

"V2A" Markers/Commands (i.e., from vLP to aLP)

| Marker | Description | Result in aLP |
|---|---|---|
| VS | Notification of a sensed event in ventricle | Initiate PVARP |
| VP | Notification of a paced event in ventricle | Initiate PVAB Initiate PVARP |
| AP | Command to deliver immediate pace pulse in atrium | Deliver immediate pace pulse to atrium |

As shown in Table 3, when the vLP senses a ventricular event, the vLP transmits an event message including a VS event marker, in response to which the aLP may initiate a PVARP interval timer. When the vLP delivers or is about to deliver a pace pulse in the ventricle, the vLP transmits VP event marker. When the aLP receives the VP event marker, the aLP initiates the PVAB interval timer and also the PVARP interval timer. The aLP may also blank its sense amplifiers to prevent possible crosstalk sensing of the remote pace pulse delivered by the vLP. The vLP may also transmit an event message containing an AP command marker to command the aLP to deliver an immediate pacing pulse in the atrium upon receipt of the command without delay.

The foregoing event markers are examples of a subset of markers that may be used to enable the aLP and vLP to maintain full dual chamber functionality. In one embodiment, the vLP may perform all dual-chamber algorithms, while the aLP may perform atrial-based hardware-related functions, such as PVAB, implemented locally within the aLP. In this embodiment, the aLP is effectively treated as a remote 'wireless' atrial pace/sense electrode. In another embodiment, the vLP may perform most but not all dual-chamber algorithms, while the aLP may perform a subset of diagnostic and therapeutic algorithms. In an alternative embodiment, vLP and aLP may equally perform diagnostic and therapeutic algorithms. In certain embodiments, decision responsibilities may be partitioned separately to one of the aLP or vLP. In other embodiments, decision responsibilities may involve joint inputs and responsibilities.

In the event that LP to LP (i2i) communication is lost (prolonged or transient), the system 100 may automatically revert to safe ventricular-based pace/sense functionalities as the vLP device is running all of the necessary algorithms to independently achieve these functionalities. For example, if the vLP loses i2i communication it may revert from the VDD mode to a VVI mode or a VDI mode, and if the aLP loses i2i communication it may revert from ADD mode to an OAO mode or an AAI mode. Thereafter, once i2i communication is restored, the system 100 can automatically resume dual-chamber functionalities.

As noted above, when using a pair of LPs (e.g., 102, 104) to perform pacing and/or sensing operations in the RA and RV, one of the challenges is that i2i communication may be relied upon to maintain appropriate synchrony between the RV and the RA.

As also noted above, a transmitter (e.g., 118) of an LP 102, 104 may be configured to transmit event messages in a manner that does not inadvertently capture the heart in the chamber where LP 102, 104 is located, such as when the associated chamber is not in a refractory state. In addition, an LP 102, 104 that receives an event message may enter an "event refractory" state (or event blanking state) following receipt of the event message. The event refractory/blanking state may be set to extend for a determined period of time after receipt of an event message in order to avoid the receiving LP 102, 104 from inadvertently sensing another signal as an event message that might otherwise cause retriggering. For example, the receiving LP 102, 104 may detect a measurement pulse from another LP 102, 104. The amplitude of a detected (i.e., sensed) measurement pulse can be referred to as the sensed amplitude.

As noted above, it has been observed that i2i conductive communication can be adversely affected by the orientation of the LPs relative to one another. Both computer simulations and animal testing have showed that sensed i2i amplitude varied widely with different orientation angles. For example, where a first LP (e.g., 102) transmits a conductive communication pulse having a pulse amplitude of 2.5V to a second LP (e.g., 104), the sensed amplitude of the pulse received by the second LP (e.g., 104) could vary from about 2 mV to less than 0.5 mV, depending upon the orientation between the first and second LPs (e.g., 102 and 104). For example, where the LP 102 is implanted in or on the RA chamber, and the LP 104 is implanted in or on the RV chamber, e.g., as shown in FIG. 1A, the orientation of the LPs 102 and 104 relative to one another can change over the course of each cardiac cycle. Additionally, the orientation of the LPs 102 and 104 relative to one another can be affected by the posture of the patient. Accordingly, since the sensed amplitude of an i2i conductive communication pulse received by one LP (e.g., 104) from the other LP (e.g., 102) can significantly vary based on the orientation of the LPs relative to one another, the sense i2i amplitude can significantly vary depending upon the timing of when an i2i conductive communication pulse is transmitted during a cardiac cycle, as well as the posture of the patient when the pulse is transmitted.

Assume, for example, that an LP 102, 104 has a 0.5 mV i2i sense threshold, meaning that a sensed pulse must have an amplitude of at least 0.5 mV in order to be detected as a communication pulse by the receiving LP. In other words, if sensed amplitudes of received communication pulses are below the sense threshold, the receiving LP will fail to receive the information encoded therein and may fail to respond accordingly, which is undesirable.

Figure 5:
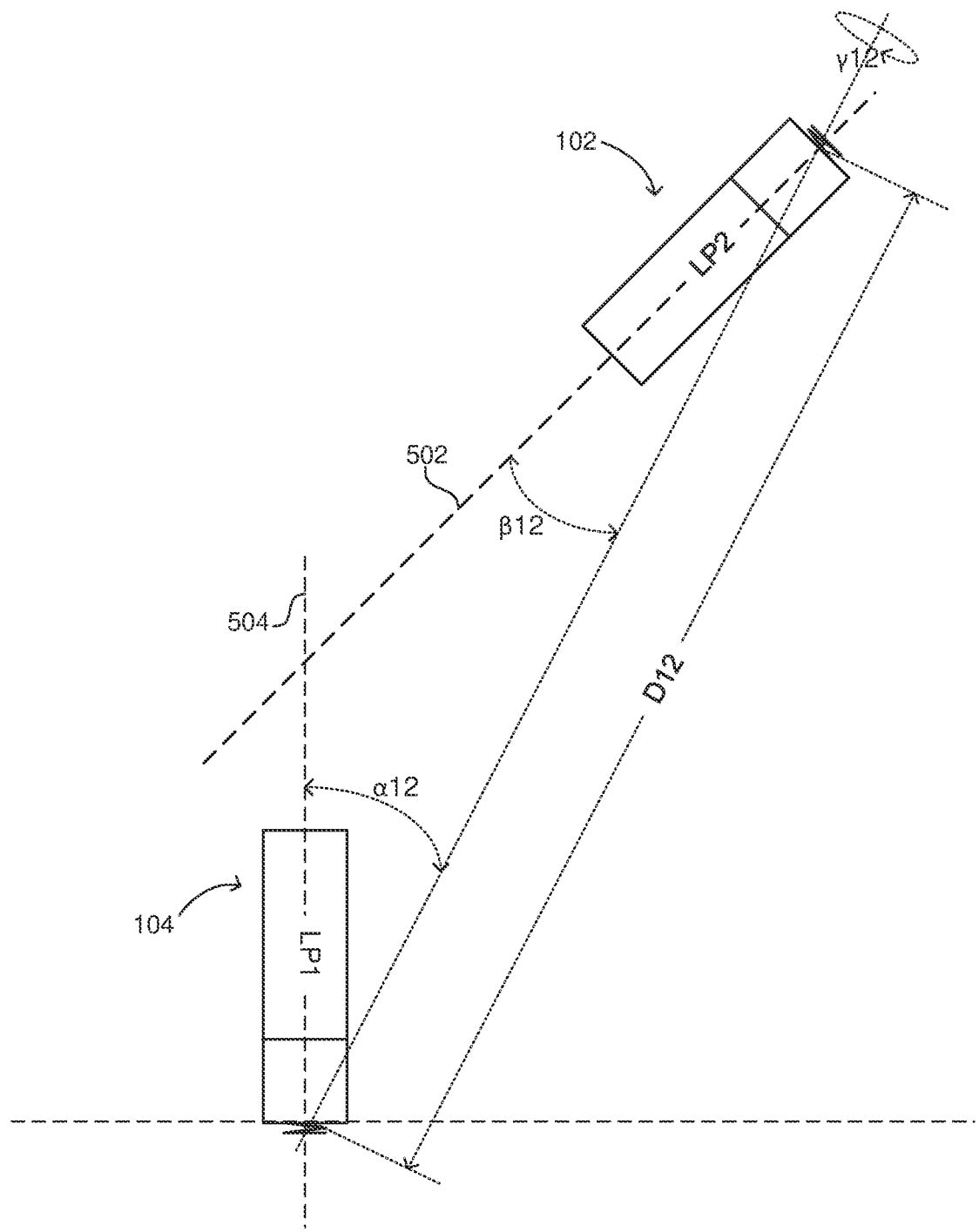
FIG. 5 is a diagram that is used to show how the orientation of two different LPs can be quantified and can affect i2i communication.

FIG. 5 is a diagram that is used to show how the orientation of two different LPs (e.g., 102, 104), labeled LP2 and LP1 in FIG. 5, can be quantified. Referring to FIG. 5, the LP2 (e.g., 102) is shown as having an axis 502, and the LP1 (e.g., 104) is shown as having an axis 504. The line D12 represents the distance between the LP1 and the LP2. In FIG. 5, the angle α12 is the angle between the axis 504 of the LP1 and the line D12; the angle β12 is the angle between the axis 502 of the LP2 and the line D12; and the angle γ12 is angle between the plane defined by the angle α12 and the plane defined by the angle β12.

Table 3, below, provides the results of simulations that show how sensed amplitudes are affected by the orientation of LP1 and LP2 relative to one another, where the LP2 is assumed to be implanted in the RA chamber, the LP1 is assumed to be implanted in the RV chamber, and the distance D12 is assumed to be fixed at 124 millimeters (mm).

TABLE 4

| Distance D12 | Angle α12 | Angle β12 | RA → RV | RA ← RV |
|---|---|---|---|---|
| 124 mm | 20° | 12° | 2.5 V → 2.13 mV | 2.11 mV ← 4-2.5 V |
| 124 mm | 20° | 32° | 2.5 V → 1.82 mV | N/A |
| 124 mm | 20° | 52° | 2.5 V → 1.32 mV | N/A |
| 124 mm | 20° | 72° | 2.5 V → 0.745 mV | N/A |
| 124 mm | 20° | 82° | 2.5 V → 0.470 mV | 0.460 mV ← 4-2.5 V |
| 124 mm | 20° | 92° | 2.5 V → 0.198 mV | 0.198 mV ← 4-2.5 V |
| 124 mm | 10° | 82° | 2.5 V → 0.6627 mV | N/A |
| 124 mm | 40° | 82° | 2.5 V → −0.1135 mV | N/A |

The first row of Table 4 shows that when the angle β12 (i.e., the angle between the axis 502 of the LP2 and the line D12) is 12 degrees, in response to the LP2 transmitting a communication pulse having an amplitude of 2.5V, the sense amplitude of the communication pulse received by the LP1 will be 2.13 mV, which is well above a 0.5 mV sense threshold. By contrast, the sixth row of Table 4 shows that when the angle β12 is 92 degrees, in response to the LP2 transmitting a communication pulse having an amplitude of 2.5V, the sense amplitude of the communication pulse received by the LP1 will be only 0.198 mV, which is well below the 0.5 mV sense threshold. Looking at the right most column and the first row of Table 4 shows that when the angle β12 is 12 degrees, in response to the LP1 transmitting a communication pulse having an amplitude of 2.5V, the sense amplitude of the communication pulse received by the LP2 will be 2.11 mV, which is well above a 0.5 mV sense threshold; and when the angle β12 is 92 degrees, in response to the LP1 transmitting a communication pulse having an amplitude of 2.5V, the sense amplitude of the communication pulse received by the LP2 will be only 0.198 mV, which is well below the 0.5 mV sense threshold.

With larger heart sizes, the sensed amplitudes decrease. More specifically, a larger heart can cause the distance D12 between the LP1 and the LP2 to increase, with the results summarized in Table 5, below.

TABLE 5

| Distance D12 | Angle α12 | Angle β12 | RA → 22 RV | RA ← RV |
|---|---|---|---|---|
| 150 mm | 20° | 12° | 2.5 V → 0.96 mV | N/A |
| 150 mm | 20° | 32° | 2.5 V → 0.76 mV | N/A |
| 150 mm | 20° | 52° | 2.5 V → 0.51 mV | N/A |
| 150 mm | 20° | 72° | 2.5 V → 0.25 mV | N/A |
| 150 mm | 20° | 82° | 2.5 V → 0.12 mV | N/A |
| 150 mm | 20° | 92° | 2.5 V → 0.005 mV | N/A |
| 150 mm | 20° | 52° | 2.5 V → 0.51 mV | N/A |

TABLE 5-continued

| Distance D12 | Angle α12 | Angle β12 | RA → 22 RV | RA ← RV |
|---|---|---|---|---|
| 150 mm | 10° | 52° | 2.5 V → 0.59 mV | N/A |
| 150 mm | 40° | 52° | 2.5 V → 0.27 mV | N/A |

The results summarized in Table 5 mimic a worst case where the heart size is at the upper bounds (D12~150 mm). As can be appreciated from a comparison between Table 5 and Table 4, the sensed amplitudes decreased as D12 was increased from 124 mm to 150 mm, so that in Table 5 when the angle β12 is greater than 52 degree, the sensed amplitude is lower than the 0.5 mV sense threshold. Accordingly, it can be appreciated that i2i communications between LPs implanted in larger hearts are even more adversely affected than smaller hearts by the relative orientation of the LPs.

When performing i2i conductive communication, the one or more pulses that are transmitted from one LP to another LP can be referred more generally as the i2i conductive communication signal. Due to the nature of electrode potential distribution, bipolar sensing of the i2i conductive communication signal (by the LP that is receiving/sensing the i2i signal) is minimal along iso-potential lines and maximum along lines orthogonal to the iso-potential lines. In other words, when the respective axes (e.g., 502 and 504 in FIG. 5) of the two LPs (communicating with one another) are aligned with one another the sensed i2i conductive communication signal is near its maximum, and when the respective axes (e.g., 502 and 504 in FIG. 5) of the two LPs are orthogonal to one another the sensed i2i conductive communication signal is near its minimum.

For the purpose of this discussion, when the LPs are oriented relative to another such that (for a give transmitted communication pulse amplitude) the sense amplitude of the communication pulse received by an LP will be below the sense threshold (e.g., 0.5 mV), the LPs can be said to be within a "deaf zone". This is because under such circumstances the LPs cannot successfully communicate or "hear" one another even though they are attempting to communicate or "talk" with one another.

Use of Far-Field and/or Sensor Signals to Supplement or Replace i2i Messaging

Figure 6A:
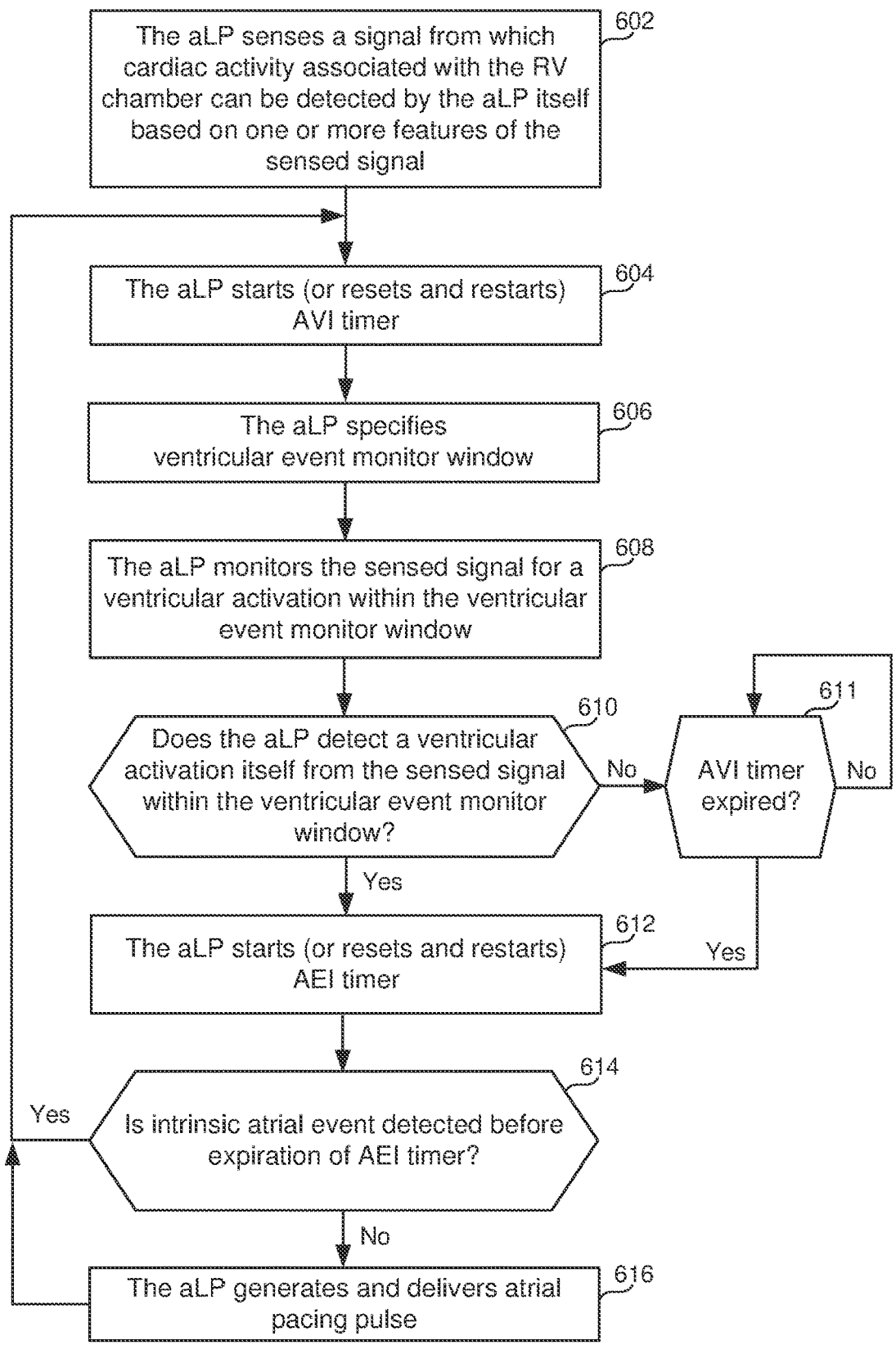
FIG. 6A is a high level flow diagram that is used to summarize methods according to certain embodiments of the present technology.

Certain embodiments of the present technology enable an aLP (e.g., 102) to detect an intrinsic or paced ventricular activation itself from a sensed signal (sensed by the aLP), without relying i2i conductive communication messaging from a vLP (e.g., 104), which i2i communication as explained above may be adversely affected by the relative orientation of the aLP and the vLP. Accordingly, such an aLP may be more robust than one that relies on receiving i2i conductive communication messages to determine when ventricular activations occur. Certain embodiments of the present technology also relate to techniques for determining an appropriate search window that the aLP should use to monitor for and detects an intrinsic or paced ventricular activation itself from a sensed signal, wherein such a search window can be referred to herein more specifically as a ventricular event monitor window. The high level flow diagram of FIG. 6A will initially be used to summarize certain methods of such embodiments. More specifically, the methods summarized with reference to FIG. 6A are for use with an implantable system including at least an aLP (e.g., 102) configured to be implanted in or on a RA chamber of a patient's heart. Depending upon the specific implementation, such an implantable system may or may not also include a vLP (e.g., 104) configured to be implanted in or on a RV chamber of the patient's heart. For much of the remaining discussion, it is assumed that a vLP is indeed implanted in or on the RV chamber of the same patient within which the aLP is implanted in or on the RV chamber.

In certain embodiments described herein, the aLP's timing is controlled either from sensing an intrinsic atrial event (known as a P-wave) or from an atrial pacing event. An intrinsic atrial event is also referred to herein as an atrial sensed (AS) event, or more succinctly as an AS. An atrial pacing event is also referred to herein as an atrial paced (AP) event, or more succinctly as an AP. In response to an AS event or an AP event, the aLP may cause two separate timers that operate in parallel to start. More specifically, the aLP can include a first timer that defines an atrial escape interval (AIE), which, if timed-out, results in an atrial paced event. This first timer can be referred to as the atrial escape interval (AIE) timer. A second timer, which may be included in a vLP, can define an AV delay, which, if timed-out, results in a ventricular paced event. This second timer may be referred to as the AV interval timer. These timers can both be started in response to a sensed or paced atrial activity, i.e., in response to an AS or AP event. The AV delay timer does not affect the AEI timer. The AEI timer thus controls the basic functioning rate of the aLP from atrial to atrial event. The ventricle is paced by the vLP, if needed, at a rate that tracks the sensed atrial rate. If no atrial activity is sensed, then the atrium is also paced by the aLP at a rate equal to the set rate. A third timer, which can be referred to as a ventricular event monitor window (VEMW) timer, can be included in the aLP and can be used to define a ventricular event monitor window (VEMW), which is a temporal window within which the aLP monitors a signal (sensed by the aLP) for a ventricular activation, as explained in more detail below. The start or starting of a timer, as the terms are used herein, can include the resetting and restarting of a timer that had already been started but had not yet timed out.

Referring to FIG. 6A, step 602 involves the aLP (e.g., 102) sensing a signal from which cardiac activity associated with the RV chamber can be sensed. Additional details of step 602, according to various embodiments of the present technology, are discussed below.

At step 604, the aLP starts an atrio-ventricular interval (AVI) timer of the aLP, in response to the aLP determining that an atrial activation occurred, which can be either an intrinsic are paced atrial activation. The AVI timer is used to determine whether a programmed atrio-ventricular interval has ended, wherein from a perspective of the aLP the atrio-ventricular interval is the maximum time interval within which a ventricular event must be detected (following an intrinsic or paced atrial activation) before the aLP presumes a ventricular activation (either intrinsic or paced) occurred but was not detected by the aLP. Such an AVI timer can be implemented by a controller (e.g., 112) of the aLP, or by a discrete timer circuit (not shown) that is communicatively coupled to the controller, but is not limited thereto. Depending upon the specific implementation, the AVI timer can be configured to start at zero and count up to a programmed atrial escape interval value, or alternatively can be configured to start at the programmed atrial escape interval value and then count down to zero. The other timers mentioned herein can be implemented in similar manners.

Step 606 involves the aLP specifying a ventricular event monitor window, which can include specifying when the ventricular event monitor window starts, and can include specifying the duration of the ventricular event monitor window, and thereby when the ventricular event monitor window ends. Additional details of the ventricular event monitor window, according to specific embodiments, are discussed below.

Step 608 involves the aLP (e.g., 102) monitoring for an intrinsic or paced ventricular activation within the ventricular event monitor window. As noted above, further example details of such a window are discussed below. At step 610 there is a determination of whether the aLP detects an intrinsic or paced ventricular activation (aka a VS or VP) itself from the sensed signal within the ventricular event monitor window, before the AVI timer times out. In accordance with certain embodiment, the ventricular event monitor window is specifically defined to end before the AVI timer times out. One way to achieve this is to ensure that the ventricular event monitor window times out before the AVI timer times out.

If the answer to the determination at step 610 is Yes, then flow goes to step 612. At step 612, the aLP starts (or resets and restarts) the AEI timer. The AEI timer is used to determine whether a programmed atrial escape interval is reached, wherein an atrial escape interval is the maximum time interval within which an AS event must be detected (following an intrinsic or paced ventricular activation) before an atrial pacing pulse will be delivered. Such an AEI timer can be implemented by a controller (e.g., 112) of the aLP, or by a discrete timer circuit (not shown) that is communicatively coupled to the controller, but is not limited thereto. Depending upon the specific implementation, the AEI timer can be configured to start at zero and count up to a programmed atrial escape interval value, or alternatively can be configured to start at the programmed atrial escape interval value and then count down to zero. The other timers mentioned herein can be implemented in similar manners. Additional timers can also be started at this point, such as the PVAB and/or PVARP timers, but not limited thereto.

If the answer to the determination at step 610 is No, then flow goes to step 611, before eventually going to step 612 once the AVI timer expires. Flow then goes to step 614 after step 612 is performed. At step 614 there is a determination of whether an intrinsic atrial event is detected by the aLP before expiration of the AEI timer.

If the answer to the determination at step 614 is No, then at the expiration of the AEI timer the aLP generates and delivers an atrial pacing pulse to the RA chamber. If the answer to the determination at step 614 is Yes, then there is no need to pace the atrium during the current cardiac cycle (because there was an intrinsic atrial activation within the cardiac cycle), and flow returns to step 604 and the AVI timer is reset and restarted.

In accordance with certain embodiments, the signal sensed by the aLP at step 602 is an electrogram (EGM) from which cardiac activity associated with the RA and RV chambers can be detected. More specifically, the aLP can detect an AS event by detecting a P-wave, and the aLP can detect an VS event by detecting a far-field R-wave. The aLP can also detect a VP event based on the EGM. In other words, where the signal sensed by the aLP at step 604 is an EGM, the aLP can monitor for a far-field R-wave (corresponding to an intrinsic ventricular activation), or a V-pulse (corresponding to a paced ventricular activation) at step 606. An R-wave or V-pulse can be detected from an EGM by comparing a magnitude of the far-field EGM, within the ventricular event monitor window, to an appropriate threshold to detect a threshold crossings indicative of an R-wave or V-pulse. Alternatively, or additionally, a far-field R-wave or V-pulse can be detected from an EGM by comparing the morphology of a portion of the EGM within the ventricular event monitor window to one or more morphological templates, including, but not limited to, a far-field R-wave template, a far-field V-pulse template, and/or a far-field paced ventricular activation template.

In accordance with certain embodiments, at step 608 the aLP monitors for an intrinsic or paced ventricular activation by determining whether a magnitude associated with one or more features of the sensed signal is above a threshold level within the ventricular event monitor window. If the threshold level is set too low there will be false detections due to oversensing. The threshold level can be a predetermined level. Alternatively the threshold level can be dynamic, e.g., can be a specified percentage (e.g. 50%) of a measured peak amplitude within an immediately preceding ventricular event monitor window, or a specified percentage (e.g., 50%) of a running average of the measured peak amplitudes within an immediately preceding plurality of (e.g. ten) ventricular event monitor windows, but is not limited thereto. Such a threshold level can be equal to or greater than a noise level, wherein the noise level can be a predetermined level, or can be a measured level. Alternatively, or additionally, at step 608 the aLP can monitor for an intrinsic or paced ventricular activation by analyzing a morphology of one or more features of the sensed signal within the ventricular event monitor window. More specifically, far-field ventricular activation templates can be stored in the memory of the aLP for both intrinsic and paced ventricular activations, and can be used by the aLP to detect intrinsic and paced ventricular activations. Other variations are also possible and within the scope of the embodiments described herein.

In accordance with alternative embodiments, the signal that is sensed by the aLP at step 602 can be produced using an accelerometer (e.g., 154) or pressure sensor (e.g., 156) of the aLP. In certain such embodiments, the signal producing using an accelerometer or pressure sensor can be used by the aLP to detect heart sounds associated with the RV chamber within the ventricular event monitor window, which heart sounds are indicative of an intrinsic or paced ventricular activation. Heart sounds are the noises generated by the beating heart and the resultant flow of blood, and are typically referred to as S1, S2, S3 and S4. Depending upon which heart sound is being detected, the LP1 can appropriately time its pacing therapy. The S1 heart sound, which is typically the loudest and most detectable of the heart sounds, is caused by the sudden block of reverse blood flow due to closure of the atrioventricular valves (mitral and tricuspid) at the beginning of ventricular contraction. Isovolumic relaxation (IR) occurs during ventricular diastole and is demarcated approximately by closure of the aortic valve and the second heart sound (S2) and approximately by opening of the mitral valve and the third heart sound (S3), which is more prominent in children and those with abnormal ventricular function when compared to normal adults. The onset of isovolumic relaxation time commences with aortic valve closure, which can be identified by the aortic component (A2) of the second heart sound (S2). The third heart sound (S3) has been linked to flow between the left atrium and the left ventricle, more generally LV filling, and thought to be due to cardiohemic vibrations powered by rapid deceleration of transmitral blood flow. The fourth heart sound (S4) may be present in the late stage of diastole and associated with atrial contraction, or kick, where the final 20% of the atrial output is delivered to the ventricles. Depending upon the specific implementation, the aLP can detect a ventricular activation within the ventricular event monitor window by detecting the S1 heart sound and/or the S2 heart sound.

Alternatively, or additionally, the aLP can detect mechanical cardiac activity associated with the RV chamber based on the signal producing using an accelerometer or pressure sensor, in order to detect an intrinsic or paced ventricular activation within the ventricular event monitor window. An intrinsic or paced ventricular activation can be detected from such a sensed signal by comparing the magnitude of the sensed signal within the ventricular event monitor window to a corresponding threshold, and/or by comparing the morphology of such a sensed signal within the ventricular event monitor window to one or more stored morphological templates.

More generally, at steps 608 and 610 the aLP can monitor the sensed signal for an intrinsic or paced ventricular activation within the ventricular event monitor window by determining whether a magnitude associated with one or more features of the sensed signal is above a specified threshold level within the ventricular event monitor window. Additionally, or alternatively, at step 608 and 610 the aLP can monitor the sensed signal for an intrinsic or paced ventricular activation within the ventricular event monitor window by analyzing a morphology of one or more features of the sensed signal within the ventricular event monitor window.

Certain embodiments of the present technology relate to specifying an appropriate start of the ventricular event monitor window during which the aLP monitors for an intrinsic or paced ventricular activation based on a signal that the aLP senses itself. Defining an appropriate start of this window is important so as to avoid mistakenly detecting atrial activations or other non-ventricular activations as ventricular activations, i.e., to minimize false positives. In certain embodiments, the ventricular event monitor window is set to start at an atrial-to-ventricular interval minus a specified delta. In other words, in such an embodiment that the aLP can start the ventricular event monitor window at a specified atrial-to-ventricular interval minus the specified delta, following a paced or sensed atrial activation. An example value for the delta is 20 milliseconds (ms), but the delta can more generally be a specified and programmed value in the range of about 10 ms to 30 ms.

Figure 6B:
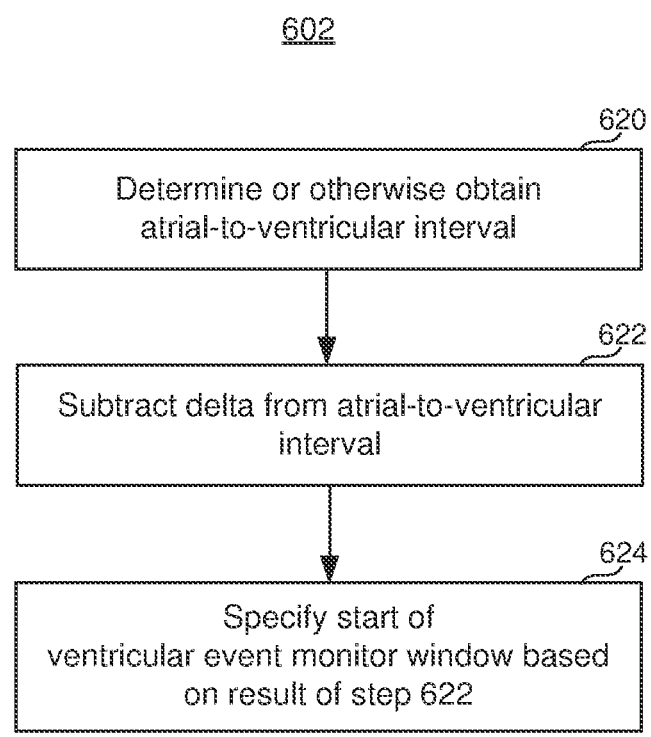
FIG. 6B is a high level flow diagram that is used to explain how one of the steps introduced in FIG. 6A can be implemented in accordance with certain embodiments of the present technology.

The high level flow diagram of FIG. 6B is used to summarize how the ventricular event monitor window can be specified by the aLP at an instance of step 602. Referring to FIG. 6B, step 620 involves determining or otherwise obtaining an atrial-to-ventricular interval. Step 622 involves subtracting a specified delta from the atrial-to-ventricular interval. Step 624 involves specifying the start of the ventricular event monitor window based on the result of the subtracting performed at step 622.

The atrial-to-ventricular interval (from which the delta is subtracted to define the start of the ventricular event monitor window) can be an AR-interval, which is the time between a paced atrial activation and a following intrinsic ventricular activation. In another embodiment, the atrial-to-ventricular interval (from which the delta is subtracted to define the start of the ventricular event monitor window) is a PR-interval, which is the time between an intrinsic atrial activation and a following intrinsic ventricular activation. In still another embodiment, the atrial-to-ventricular interval (from which the delta is subtracted to define the start of the ventricular event monitor window) is an AV-interval, which is a time between a paced atrial activation and a following paced ventricular activation. In a further embodiment, the atrial-to-ventricular interval (from which the delta is subtracted to define the start of the ventricular event monitor window) can be an AR-interval, which is a time between a paced atrial activation and a following intrinsic ventricular activation. In accordance with certain embodiments, where the aLP has both an AV-interval and an AR-interval stored within memory or registers of the aLP, the ventricular event monitor window is the shorter of these two intervals minus the specified delta. In accordance with certain embodiments, where the aLP has both a PV-interval and a PR-interval stored within memory or registers of the aLP, the ventricular event monitor window is the shorter of these two interval minus the specified delta.

Where the atrial-to-ventricular interval obtained at step 620 is an AR-interval, it can be the AR-interval measured during a previous cardiac cycle, or an average of the N previous AR-intervals measured during the previous N cardiac cycles, where N is an integer that is at least two. Such an average can be a simple average or a weighted average. Similarly, where the atrial-to-ventricular interval obtained at step 620 is a PR-interval, it can be the PR-interval measured during a previous cardiac cycle, or a simple or weighted average of the N previous PR-intervals measured during the previous N cardiac cycles, where N is an integer that is at least two. The atrial-to-ventricular interval obtained at step 620 can also be an average of a combination of PR and AR-intervals.

The aLP can use a timer to determine when the ventricular event monitor window is to start, wherein when this timer times out the ventricular event monitor window is started. Such a timer can be referred to as a ventricular event monitor window start timer. Depending upon the specific implementation, such a timer can be started as soon as the magnitude of the EGM exceeds an atrial sensitivity threshold (e.g., 704 in FIG. 7A) that is used to detect atrial activations, or more specifically used to detect P-waves. Alternatively, this timer can be started at an end of a P-wave detected by the aLP, at a peak of a P-wave, or at a further specified delta after the end or peak of the P-wave detected by the aLP. This timer can alternatively be started at an A-pace delivered by the aLP, or at a further specified delta after the A-pace delivered by the LP. A further timer, which can be referred to as a ventricular event monitor window timer, can be started when the ventricular event monitor window start timer times out, and can be used by the aLP to determine when the ventricular event monitor window ends. Depending upon the specific implementations, these aforementioned timers can be configured to start at zero and count up to a respective programmed value, or alternatively can be configured to start at the programmed value and then count down to zero. Such timers can be implemented by a controller (e.g., 112) of the aLP, or by discrete timers communicatively coupled to the controller, but are not limited thereto. The length of the ventricular event monitor window can be programmed into the aLP prior to implant, at implant, or at patient follow-ups during which a communication session occurs between the aLP and an external patient programmer (e.g., 109). An example programmed value for the ventricular event monitor window is 275 ms, although longer or shorter windows are also possible. In accordance with certain embodiments, the aLP shuts off at least one of its receivers (e.g., 120 and/or 122 in FIG. 1B) of the aLP during each ventricular event monitor window to thereby conserve energy.

In accordance with certain embodiments, the ventricular event monitor window is rate adaptive. As explained above, the start of the ventricular event monitor window can be based on atrial-to-ventricular interval (e.g., one of a PR-interval, an AR-interval, a PV-interval, or an AV-interval, minus a specified delta). If a rate responsive atrial-to-ventricular interval is enabled, the higher the patient's heart rate (HR) the shorter the atrial-to-ventricular interval, thereby making the start of the ventricular event monitor window rate adaptive. The aLP can have a programmed base atrial-to-ventricular interval (e.g., 150 ms) and a programmed minimum (i.e., shortest) atrial-to-ventricular interval (e.g., 50 ms). Depending on the patient's HR, the patient's actual atrial-to-ventricular interval is somewhere between the base and minimum values. For example, if the patient's HR is 60 bpm (base rate), the base atrial-to-ventricular interval (e.g., 150 ms) can be used. If the patient's HR goes up to 80 bpm, then the atrial-to-ventricular interval can become 100 ms. If the patient's HR goes up to 100 bpm, then the atrial-to-ventricular interval may reach its minimum (i.e., shortest) value (e.g., 50 ms). How fast the interval decrements can depend on a gain factor (e.g., there can be low, medium, or high gain factors), which can also programmable. Where the aLP is already capable of rate responsive (also known as rate adaptive) pacing, e.g., based on outputs of an accelerometer and/or temperature sensor, such outputs can also be used to make the start of the ventricular event monitor window rate adaptive. Alternatively, the aLP can utilize an algorithm to make the start of the ventricular event monitor window rate adaptive, wherein the algorithm is independent of the atrial-to-ventricular interval.

In accordance with a specific embodiments, as the atrial-to-ventricular interval changes, a slope or ratio of the atrial-to-ventricular interval relative to a baseline atrial-to-ventricular interval can be determined, and that slope or ratio (or an indicator thereof) can be used as a scaling factor that is used to specify the start of the ventricular event monitor window and/or the duration of the ventricular event monitor window. The start and/or duration of the ventricular event monitor window can alternatively or additionally be rate adaptive based on changes in an atrial cycle length. In accordance with a specific embodiments, as the atrial cycle length changes, a slope or ratio of the atrial cycle length relative to a baseline atrial cycle length can be determined, and that slope or ratio (or an indicator thereof) can be used as a scaling factor that is used to specify the start and/or duration of the ventricular event monitor window. More generally, the start and/or duration of the ventricular event monitor window can be made rate adaptive by adjusting the start and/or duration based on a measure of HR, atrial cycle length, or some measure of activity, e.g., as measured from an accelerometer and/or temperature sensor, but not limited thereto.

Where the implantable system (including the aLP that implements the method summarized with reference to the flow diagram of FIG. 6A) also includes a vLP configured to be implanted in or on the RV chamber of the patient's heart, the aLP can receive i2i messages that are transmitted by the vLP, as was described above with reference to FIGS. 1A through 4. Such i2i messages can be used by the vLP to inform the aLP of any premature ventricular contractions (PVCs) that the vLP detects. In such an embodiment, the aLP, in response to receiving an i2i message from the vLP that informs the aLP of a PVC detected by the vLP, the aLP can time its delivery of an atrial pacing pulse to the RA chamber based on when the PVC occurred, rather than based on a ventricular activation that the aLP detects based on a signal the aLP sensed itself. Such an i2i message can be received by the aLP using one or more receivers (e.g., 120, 122) of the aLP.

In accordance with certain embodiments, the aLP can measure the maximum amplitudes (within the ventricular event monitor windows) of peaks of the signal it senses at instances of step 604 in order to determine whether the maximum amplitudes of such peaks are above a specified noise level, e.g., above 0.1 mV, or more generally above a specified threshold. So long as the maximum amplitudes of such peaks (within the ventricular event monitor windows) are above the specified threshold (e.g., a noise level threshold), the aLP will monitor for ventricular activations based on the signal the aLP senses itself at instances of step 604, and will time its selective atrial pacing relative to the ventricular activations that the aLP detects based on the signal it senses itself. However, when the aLP determines that the maximum amplitudes of peaks of the sensed signal (within the ventricular event monitor windows) are not above the specified noise level for a specified number of cardiac cycles (e.g., 1, 2, or 3 cardiac cycles), then the aLP may send an i2i instruction or request message to the vLP, requesting that the vLP send an i2i message to the aLP to inform the aLP of intrinsic and/or paced ventricular activations. Such an i2i message that the vLP sends to the aLP can be an implant event message including an event marker indicative of a nature of the event (e.g., intrinsic/sensed ventricular event, paced ventricular event) and the timing of the event. Alternatively, the vLP can send such event marker i2i messages to the aLP whenever intrinsic or pace ventricular activations occur, but the aLP can disable one or more of its receiver(s) to conserve power so long as the maximum amplitudes of peaks of the signal sensed by the aLP is above the specified noise level (or more generally, above a specified threshold), and the aLP can selectively turn on its receiver(s) when the maximum amplitudes of peaks of the signal sensed by the aLP is not above the specified noise level (or more generally, not above the specified threshold). In this manner, the aLP can conserver power when appropriate by selectively disabling its receiver(s) when able to, and enabling its receiver(s) when the aLP realizes it needs to rely on i2i messages for appropriately timing its selectively atrial pacing. Such pacing is referred to as "selective" atrial pacing, because an atrial pacing pulse is only delivered when an intrinsic atrial event is not detected within the atrial escape interval. The above described embodiments can be used to provide for a hybrid of relying on far-field sensing and i2i messaging to detect ventricular activations in order to balance battery usage of the aLP and the vLP. More generally, in accordance with certain embodiments, where an implantable system includes at least an aLP and a vLP, in order to balance the battery usage of the two (or more) LPs, a hybrid of relying on far-field sensing and i2i messaging can be used to identify activations in remote cardiac chambers.

Figure 7A:
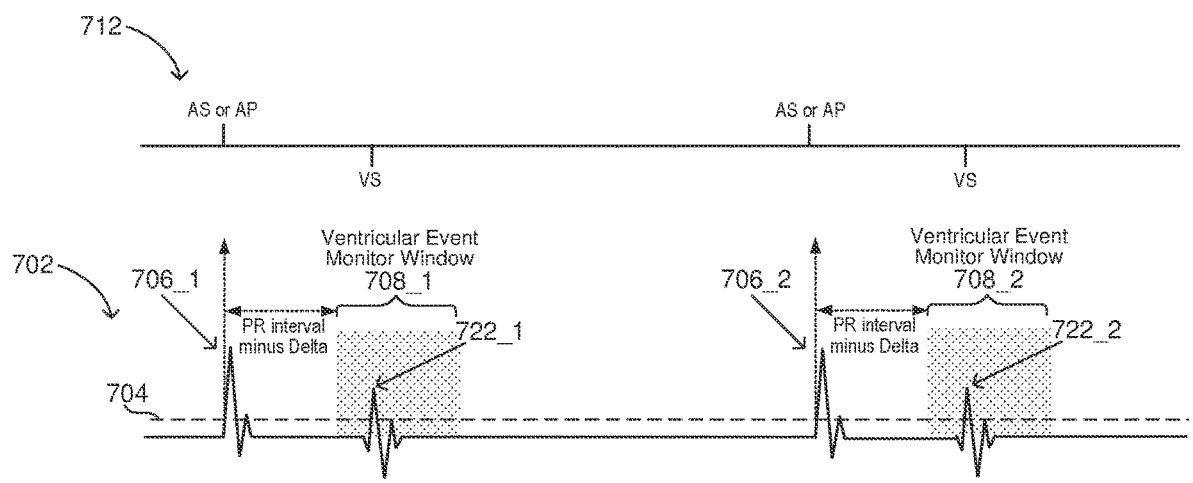
FIG. 7A includes is an example of an electrogram (EGM) sensed by an atrial leadless pacemaker (aLP) and is used to explain in more detail how the embodiments summarized with reference to the high level flow diagram of FIG. 6A can be implemented.

FIG. 7A will now be used to explain how an embodiment of the present technology, initially summarized above with reference to the high level flow diagram of FIG. 6A, may work where the aLP monitors for ventricular activations based on an EGM that the aLP (e.g., 102) itself senses using its electrodes (e.g., 108). Referring to FIG. 7A, shown therein is an example of an EGM 702 sensed by the aLP. In a typical EGM sensed by a conventional pacemaker having leads with electrodes on the leads, P-waves that are indicative of intrinsic atrial activations have much lower amplitudes than R-waves that are indicative of intrinsic ventricular activations. However, in this case, since the aLP and its electrodes are within an atrial chamber, the P-waves (or more generally features) of the EGM that are indicative of local intrinsic atrial activations have greater amplitudes than far-field R-waves (and more generally features) that are indicative of remote intrinsic ventricular activations.

In FIG. 7A the dashed line 704 corresponds to an atrial sensitivity threshold which is used to detect atrial activations, examples of which are labeled 706_1 and 706_2. As can be appreciated from FIG. 7A, an atrial sensed (AS) event is detected when an amplitude of the EGM exceeds the atrial sensitivity threshold 704, which can be programmed and fixed, or can be dynamically adjusted. An atrial paced (AP) event need not be sensed, since the aLP knows when it delivers an atrial pacing pulse. An AS event, as noted above, is also referred to herein as an intrinsic atrial activation. An AP event, as noted above, is also referred to herein as a paced ventricular activation. Above the example EGM 702 is a marker timeline 712, which includes upward extending vertical lines labeled AS or AP, which show when atrial sensed (AS) or atrial paced (AP) events occurred. The marker timeline 712 also includes downward extending vertical lines labeled VS, which show when ventricular senses (VS) events occurred. VS events area also referred to herein as intrinsic ventricular activations, as noted above.

As can be appreciated from FIG. 7A, following the AS event 706_1, at a time equal to a PR interval minus a specified delta, begins a ventricular event monitor window 708_1 within which the aLP monitors for an intrinsic or paced ventricular activation. Similarly, following the AS event 706_2, at a time equal to the PR interval minus the specified delta, begins another ventricular event monitor window 708_2 within which the aLP monitors for an intrinsic or paced ventricular activation. As can also be appreciated from FIG. 7A, the aLP detects a ventricular activation 722_1 within the search window 708_1, and detects a ventricular activation 722_2 within the search window 708_2.

The PR interval, or other atrial-to-ventricular interval (from which the delta is subtracted to define the start of the ventricular event monitor window) is programmed into the aLP prior to implant, at implant, or at patient follow-ups during which a communication session occurs between the aLP and an external patient programmer (e.g., 109). An example programmed value for the PR interval is 200 ms. Assuming for example that the specified delta is 20 ms, and that the ventricular event monitor window starts at the PR interval minus this delta after the peak of a P-wave or the delivery of an A-pulse, then the ventricular event monitor window would start 180 ms (200 ms−20 ms=180 ms) following the peak of a P-wave or the delivery of an A-pulse. As noted above, an example length of the ventricular event monitor window is 275 ms, but longer or shorter window lengths are also possible. While using the embodiments of the present technology that are described above with reference to FIGS. 6, 7A, and 7B, there is no need for the aLP to utilize a post-ventricular atrial blanking period (PVAB), which is typically required in an LP system that utilizes i2i communication.

As explained above, in accordance with certain embodiments described herein, the aLP (e.g., 104) times its delivery of an atrial pacing pulse to the RA chamber based on the intrinsic or paced ventricular activation detected by the aLP from the sensed signal within the ventricular event monitor window comprises. More specifically, the aLP can determine an AV delay as being equal to a time between a time of an intrinsic or paced atrial activation and a time of the intrinsic or paced ventricular activation detected by the aLP from the sensed signal within the ventricular event monitor window. The aLP can then time its delivery of the atrial pacing pulse to the RA chamber a VA delay following the AV delay, wherein the VA delay can be programmed into the aLP.

Where an implantable system also includes a vLP (e.g., 104) that is capable of communicating with an aLP (e.g., 102), the aLP can use its receiver(s) (e.g., 120, 122) to detect an i2i message that is transmitted by the vLP. In certain instance, the i2i message that the aLP receives from the vLP can be a message from the vLP that informs the aLP of a premature ventricular contraction (PVC) that was detected by the vLP. In such a case, the aLP can time its delivery of an atrial pacing pulse to the RA chamber based on the PVC, rather than based on an intrinsic or paced ventricular activation that the aLP detected itself from a signal that was sensed by the aLP itself. For example, the aLP can reset and restart its AEI timer based on the PVC. In certain embodiments, the vLP can detect a PVC if the vLP detects two consecutive ventricular events without detecting a far-field P-wave between the two consecutive ventricular events. The vLP can alternatively, or additionally, detect a PVC if the vLP detects two consecutive ventricular events without receiving an i2i message from the aLP (that informs the vLP that an intervening atrial event occurred), between the two consecutive ventricular events. In such embodiments, the second of the two consecutive ventricular events can be classified as a PVC. Alternative and/or additional techniques for detecting a PVC are possible, and are within the scope of the embodiments described herein.

Figure 7B:
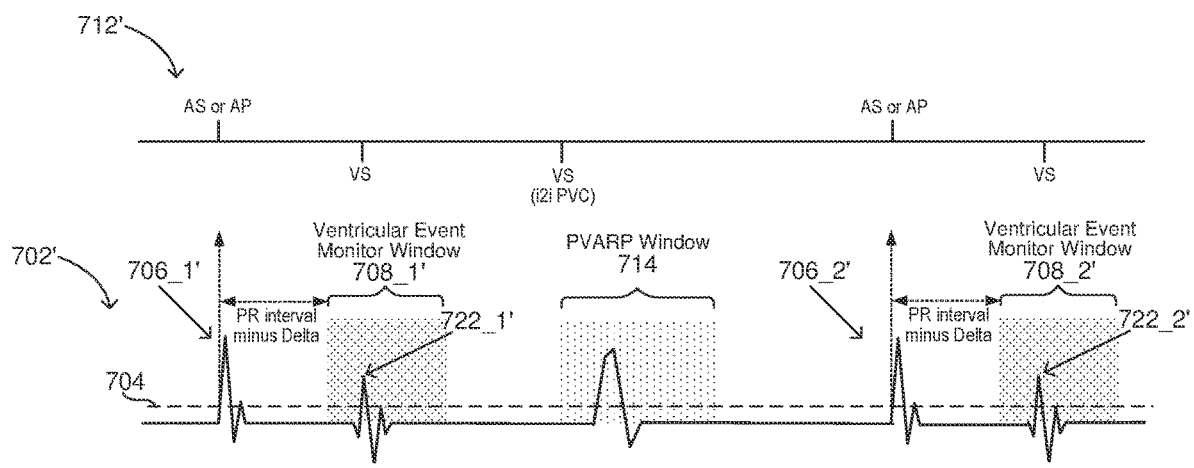
FIG. 7B includes is another example of an EGM sensed by an aLP and is used to explain how an aLP can be informed of a premature ventricular contraction (PVC) via an i2i message received from a ventricular leadless pacemaker (vLP) and respond accordingly.

FIG. 7B will now be used to explain how an aLP can be informed of a PVC via an i2i message received from a vLP and respond accordingly. Referring to FIG. 7B, shown therein is an example of an EGM 702' sensed by the aLP. As was also the case in FIG. 7A, in FIG. 7B the dashed line 704 corresponds to an atrial sensitivity threshold which is used to detect atrial activations, examples of which are labeled 706_1' and 706_2'. As can be appreciated from FIG. 7B, an atrial sensed (AS) event is detected when an amplitude of the EGM exceeds the atrial sensitivity threshold 704. Above the example EGM 702' is a marker timeline 712', which includes upward extending vertical lines labeled AS or AP, which show when atrial sensed (AS) or atrial paced (AP) events occurred. The marker timeline 712' also includes downward extending vertical lines labeled VS, which show when ventricular senses (VS) events occurred. One of the downward extending vertical lines labeled VS, is also labeled i2i PVC and corresponds to when the aLP receives an i2i message from the vLP that informs the aLP of a PVC that was detected by the vLP.

Following the AS event 706_1', at a time equal to a PR interval minus a specified delta, begins a ventricular event monitor window 708_1' within which the aLP monitors for an intrinsic or paced ventricular activation. Following the PVC if a post ventricular atrial refractory period (PVARP) window 714, which is used to prevent the aLP from sensing a retrograde P wave that might trigger a pacemaker mediated tachycardia (PMT). As an example, the PVARP window can be 480 ms (AR 150 ms and PR 330 ms), but is not limited thereto. Following the PVARP window 714 is an AS event 706_2'. Following the AS event 706_2', at a time equal to the PR interval minus the specified delta, begins another ventricular event monitor window 708_2' within which the aLP monitors for an intrinsic or paced ventricular activation. As can also be appreciated from FIG. 7B, the aLP detects a ventricular activation 722_1' within the search window 708_1', and detects a ventricular activation 722_2' within the search window 708_2'.

The aLP can itself monitor for a premature atrial contraction (PAC), and in response to detecting a PAC, the aLP can transmit an i2i message to a vLP that informs the vLP of the detected PAC. In such a case the vLP can time its delivery of a ventricular pacing pulse to the RV chamber based on the PAC. For example, the vLP can reset and restart its AV interval timer based on the PAC.

By using certain embodiments described herein an aLP need not rely on i2i communications from an aLP to determine when an intrinsic or paced ventricular activation occurs. However, where an implantable system also includes a vLP, it may be difficult for the vLP to detect far-field P-wave or the like, since they are of relatively low amplitude. Thus, the vLP may need to rely on i2i communications from the aLP to determine when an intrinsic or pace atrial activation occurs. Accordingly, where an implantable system includes both an aLP and a vLP, the aLP may transmit, each cardiac cycle, an i2i message to the vLP to inform the vLP of an intrinsic or paced atrial activation, to thereby enable the vLP to time its delivery of a ventricular pacing pulse to the RV chamber based on the intrinsic or paced atrial activation. In certain such embodiments, each i2i message that the aLP transmits to the vLP can include a status bit that informs the vLP whether the aLP was able to successfully detect an intrinsic or paced ventricular activation itself from a sensed signal (sensed by the aLP) during one or more previous cardiac cycles. In these embodiments, the vLP can determine whether or not to transmit an i2i message to the aLP based on the status bit included in one or more i2i messages that the vLP receives from the aLP. Each i2i message that the aLP transmits to the vLP can also include a second status bit that informs the vLP whether the aLP received a valid i2i message from the vLP during one or more previous cardiac cycles. In such an embodiment, the vLP can determine, based on the second status bit, whether to adjust the amplitude and/or timing of one or more further i2i messages that the vLP transmits to the aLP, in an attempt to increase the probability that the aLP successfully receives valid i2i messages from the vLP.

Figure 8:
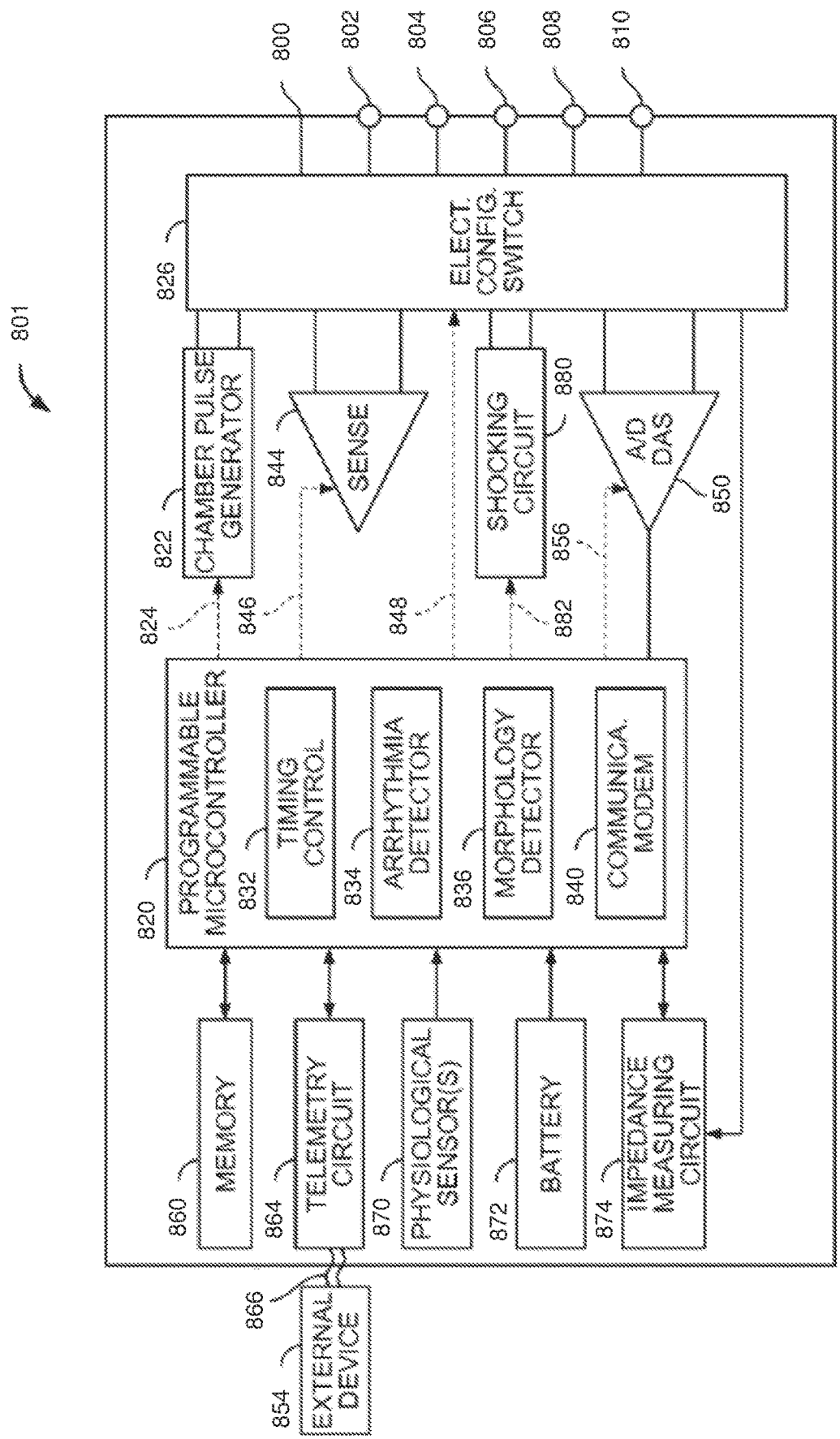
FIG. 8 shows a block diagram of an embodiment of an LP that is implanted into a patient as part of an implantable cardiac system in accordance with certain embodiments herein.

FIG. 8 shows a block diagram of showing exemplary further details of an LP 801 (e.g., 102, 104) that is implanted into the patient as part of the implantable cardiac system in accordance with certain embodiments herein. LP 801 may be implemented as a full-function biventricular pacemaker, equipped with both atrial and ventricular sensing and pacing circuitry for four chamber sensing and stimulation therapy (including both pacing and shock treatment). Optionally, LP 801 may provide full-function cardiac resynchronization therapy. Alternatively, LP 801 may be implemented with a reduced set of functions and components. For instance, the LP may be implemented without ventricular sensing and pacing.

LP 801 has a housing 800 to hold the electronic/computing components. Housing 800 (which is often referred to as the "can", "case", "encasing", or "case electrode") may be programmably selected to act as the return electrode for certain stimulus modes. Housing 800 may further include a connector (not shown) with a plurality of terminals 802, 804, 806, 808, and 810. The terminals may be connected to electrodes that are located in various locations on housing 800 or elsewhere within and about the heart. LP 801 includes a programmable microcontroller 820 that controls various operations of LP 801, including cardiac monitoring and stimulation therapy. Microcontroller 820 includes a microprocessor (or equivalent control circuitry), RAM and/or ROM memory, logic and timing circuitry, state machine circuitry, and I/O circuitry. The microcontroller is an example of a controller (e.g., 82) discussed above.

LP 801 further includes a pulse generator 822 that generates stimulation pulses and communication pulses for delivery by one or more electrodes coupled thereto. Pulse generator 822 is controlled by microcontroller 820 via control signal 824. Pulse generator 822 may be coupled to the select electrode(s) via an electrode configuration switch 826, which includes multiple switches for connecting the desired electrodes to the appropriate I/O circuits, thereby facilitating electrode programmability. Switch 826 is controlled by a control signal 828 from microcontroller 820.

In FIG. 8, a single pulse generator 822 is illustrated. Optionally, the LP may include multiple pulse generators, similar to pulse generator 822, where each pulse generator is coupled to one or more electrodes and controlled by microcontroller 820 to deliver select stimulus pulse(s) to the corresponding one or more electrodes. For example, one pulse generator can be used to generate pacing pulses, and another pulse generator can be used to generate i2i pulses.

Microcontroller 820 is illustrated as including timing control circuitry 832 to control the timing of the stimulation pulses (e.g., pacing rate, atrio-ventricular (AV) delay, atrial interconduction (A-A) delay, or ventricular interconduction (V-V) delay, etc.). Timing control circuitry 832 may also be used for the timing of refractory periods, blanking intervals, noise detection windows, evoked response windows, alert intervals, marker channel timing, and so on. The timing control circuitry 832 can also be used to time various intervals and periods mentioned above, including, but not limited to, the AVI, AEI, PVAB, PVARP, and/or the like. Microcontroller 820 may also have an arrhythmia detector 834 for detecting arrhythmia conditions and a morphology detector 836. Although not shown, the microcontroller 820 may further include other dedicated circuitry and/or firmware/software components that assist in monitoring various conditions of the patient's heart and managing pacing therapies. The microcontroller can include a processor. The microcontroller, and/or the processor thereof, can be used to perform the methods of the present technology described herein.

LP 801 is further equipped with a communication modem (modulator/demodulator) 840 to enable wireless communication with the remote slave pacing unit. Modem 840 may include one or more transmitters and one or more receivers as discussed herein in connection with FIG. 1B. In one implementation, modem 840 may use low or high frequency modulation. As one example, modem 840 may transmit i2i messages and other signals through conductive communication between a pair of electrodes. Modem 840 may be implemented in hardware as part of microcontroller 820, or as software/firmware instructions programmed into and executed by microcontroller 820. Alternatively, modem 840 may reside separately from the microcontroller as a stand-alone component.

LP 801 includes a sensing circuit 844 selectively coupled to one or more electrodes, that perform sensing operations, through switch 826 to detect the presence of cardiac activity associated with one or more chambers of the heart. Sensing circuit 844 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 826 determines the sensing polarity of the cardiac signal by selectively closing the appropriate switches. In this way, the clinician may program the sensing polarity independent of the stimulation polarity.

The output of sensing circuit 844 is connected to microcontroller 820 which, in turn, triggers or inhibits the pulse generator 822 in response to the presence or absence of cardiac activity. Sensing circuit 844 receives a control signal 846 from microcontroller 820 for purposes of controlling the gain, threshold, polarization charge removal circuitry (not shown), and the timing of any blocking circuitry (not shown) coupled to the inputs of the sensing circuitry.

In FIG. 8, a single sensing circuit 844 is illustrated. Optionally, the LP may include multiple sensing circuits, similar to sensing circuit 844, where each sensing circuit is coupled to one or more electrodes and controlled by microcontroller 820 to sense electrical activity detected at the corresponding one or more electrodes. For example, one sensing circuit can be used to sense near-field signals, another sensing circuit can be used to sense far-field signals, and one or more further sensing circuits can be used to sense i2i signals.

LP 801 further includes an analog-to-digital (A/D) data acquisition system (DAS) 850 coupled to one or more electrodes via switch 826 to sample cardiac signals across any pair of desired electrodes. Data acquisition system 850 is configured to acquire intracardiac electrogram signals, convert the raw analog data into digital data, and store the digital data for later processing and/or telemetric transmission to an external device 854 (e.g., a programmer, local transceiver, or a diagnostic system analyzer). Data acquisition system 850 is controlled by a control signal 856 from the microcontroller 820.

Microcontroller 820 is coupled to a memory 860 by a suitable data/address bus. The programmable operating parameters used by microcontroller 820 are stored in memory 860 and used to customize the operation of LP 801 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy. The programmable microcontroller 820 in FIG. 8, and the controller 112 in FIG. 1B, and are examples of a controller and/or processor that can be used to perform the methods summarized above, e.g., with reference to FIG. 6A as well as other FIGS.

The operating parameters of LP 801 may be non-invasively programmed into memory 860 through a telemetry circuit 864 in telemetric communication via communication link 866 with external device 854. Telemetry circuit 864 allows intracardiac electrograms and status information relating to the operation of LP 801 (as contained in microcontroller 820 or memory 860) to be sent to external device 854 through communication link 866.

LP 801 can further include magnet detection circuitry (not shown), coupled to microcontroller 820, to detect when a magnet is placed over the unit. A magnet may be used by a clinician to perform various test functions of LP 801 and/or to signal microcontroller 820 that external device 854 is in place to receive or transmit data to microcontroller 820 through telemetry circuits 864.

LP 801 can further include one or more physiological sensors 870. Such sensors are commonly referred to as "rate-responsive" sensors because they are typically used to adjust pacing stimulation rates according to the exercise state of the patient. However, physiological sensor 870 may further be used to detect changes in cardiac output, changes in the physiological condition of the heart, or diurnal changes in activity (e.g., detecting sleep and wake states). Signals generated by physiological sensors 870 are passed to microcontroller 820 for analysis. Microcontroller 820 responds by adjusting the various pacing parameters (such as rate, AV Delay, V-V Delay, etc.) at which the atrial and ventricular pacing pulses are administered. While shown as being included within LP 801, physiological sensor(s) 870 may be external to LP 801, yet still be implanted within or carried by the patient. Examples of physiologic sensors might include sensors that, for example, sense temperature, respiration rate, pH of blood, ventricular gradient, activity, position/posture, minute ventilation (MV), and so forth. The physiological sensors 870 can include, e.g., an accelerometer (e.g., 154 in FIG. 1B) and/or a pressure sensor (e.g., 156 in FIG. 1B).

A battery 872 provides operating power to all of the components in LP 801. Battery 872 is preferably capable of operating at low current drains for long periods of time. Battery 872 also desirably has a predictable discharge characteristic so that elective replacement time can be detected. As one example, LP 801 employs a lithium carbon monofluoride (Li-CFx) battery. In certain embodiments, examples of which were described above with reference to FIGS. 9A and 9B, the battery 872 (which was labeled 924 in FIGS. 9A and 9B) can be located in a first hermetic electrically conductive housing, and the microcontroller 820 and other circuitry can be located in a second hermetic electrically conductive housing.

LP 801 further includes an impedance measuring circuit 874, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Impedance measuring circuit 874 is coupled to switch 826 so that any desired electrode may be used. In this embodiment LP 801 further includes an optional shocking circuit 880 coupled to microcontroller 820 by a data/address bus 882.

In some embodiments, an LP is configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking & refractory periods, etc. Accordingly, each LP needs to know an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or VVI), and for the IPG to utilize the proper set of settings and algorithms (e.g., V-AutoCapture vs ACap-Confirm, sensing sensitivities, etc.).

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Aspects of the present disclosure are described herein with reference to flowchart illustrations and/or block diagrams of methods, apparatuses (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor or other programmable data processing apparatus to produce a machine, such that the instructions, which execute via the processor or other programmable instruction execution apparatus, create a mechanism for implementing the functions/acts specified in the flowchart and/or block diagram block or blocks.

The computer-readable non-transitory media includes all types of computer readable media, including magnetic storage media, optical storage media, and solid state storage media and specifically excludes signals. It should be understood that the software can be installed in and sold with the device. Alternatively the software can be obtained and loaded into the device, including obtaining the software via a disc medium or from any manner of network or distribution system, including, for example, from a server owned by the software creator or from a server not owned but used by the software creator.

Computer-readable storage media (medium) exclude (excludes) propagated signals per se, can be accessed by a processor and/or controller, and include volatile and non-volatile internal and/or external media that is removable and/or non-removable. Various types of storage media accommodate the storage of data in any suitable digital format. It should be appreciated by those skilled in the art that other types of computer readable medium can be employed such as solid state drives, flash memory cards, flash drives, cartridges, and the like, for storing computer executable instructions for performing the novel methods (acts) of the disclosed architecture.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIG. 6A. For another example, it is possible to change the boundaries of some of the dashed blocks shown in FIGS. 1B and 8.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. An atrial leadless pacemaker (aLP) configured to be implanted in or on an atrial chamber of a patient's heart, the aLP comprising:
    two or more electrodes;
    a pulse generator electrically coupled or coupleable to at least two of the two or more electrodes;
    at least one of a sensor or circuitry configured to sense a signal from which cardiac activity associated with a ventricular chamber of the patient's heart can be detected based on one or more features of the sensed signal;
    at least one of a processor or controller configured to
        control the pulse generator to selectively generate an atrial pacing pulse for delivery to the atrial chamber via at least two of the two or more electrodes;
        specify a ventricular event monitor window;
        monitor the sensed signal for a ventricular activation within the ventricular event monitor window; and
        reset an atrial escape interval timer, in response to the ventricular activation being detected from the sensed signal within the ventricular event monitor window;
        wherein the atrial escape interval timer is used to time delivery of the atrial pacing pulse to the atrial chamber if an intrinsic atrial activation is not detected within an atrial escape interval.

2. The aLP of claim 1, wherein:
    the at least one of the sensor or circuitry comprises sensing circuitry electrically coupled or coupleable to at least two of the two or more electrodes and configured to sense an electrogram (EGM);

the sensed signal, from which cardiac activity associated with the ventricular chamber of the patient's heart can be detected, comprises the EGM; and the at least one of the processor or controller is configured to monitor the EGM for a far-field R-wave or V-pulse within the ventricular event monitor window to thereby monitor for the ventricular activation, which can be intrinsic or paced.

3. The aLP of claim 1, wherein:

the at least one of the sensor or circuitry comprises an accelerometer or a pressure sensor configured to sense the signal from which cardiac activity associated with the ventricular chamber of the patient's heart can be detected based on one or more features of the sensed signal; and the at least one of the processor or controller is configured to monitor the sensed signal for a specific heart sound within the ventricular event monitor window, or for an indication of a mechanical contraction within the ventricular event monitor window, to thereby monitor for the ventricular activation, which can be intrinsic or paced.

4. The aLP of claim 1, wherein:

to specify the ventricular event monitor window the at least one of the processor or controller is configured to start the ventricular event monitor window at a specified atrial-to-ventricular interval minus a specified non-zero delta, after a paced or intrinsic atrial activation; and the specified atrial-to-ventricular interval comprises one of a PV-interval, a PR-interval, an AV-interval, or an AR-interval.

5. The aLP of claim 1, wherein to specify the ventricular event monitor window the at least one of the processor or controller is configured to:

detect an end of a P-wave that corresponds to an intrinsic atrial activation; and start the ventricular event monitor window at the end of the P-wave or a specified non-zero delta after the end of the P-wave.

6. The aLP of claim 1, wherein to specify the ventricular event monitor window:

the aLP uses a ventricular event monitor window start timer to determine when the ventricular event monitor window is to start, such that when the ventricular event monitor window start timer times out the ventricular event monitor window is started; and the at least one of the processor or controller is configured to start the ventricular event monitor window start timer in one of the following manners:

when a P-wave is detected by the aLP;

at an end of the P-wave detected by the aLP;

at a specified delta after the end of the P-wave detected by the aLP;

at a peak of the P-wave detected by the aLP;

at the specified delta after the peak of the P-wave detected by the aLP;

when a said atrial pacing pulse is delivered by the aLP; or at a further specified delta after the said atrial pacing pulse is delivered by the aLP.

7. The aLP of claim 6, wherein to specify the ventricular event monitor window:

the aLP uses a ventricular event monitor window timer, which is started when the ventricular event monitor window start timer times out, to determine when the ventricular event monitor window ends.

8. The aLP of claim 1, wherein the at least one of the processor or controller is configured to determine at least one of a start of or a duration of the ventricular event monitor window based on at least one of an atrial cycle length, a measure of temperature, or a measure of activity, so that the at least one of the start of or the duration of the ventricular event monitor window is rate adaptive.

9. The aLP of claim 1, further comprising:

one or more receivers configured to receive implant-to-implant (i2i) messages from a ventricular leadless pacemaker (vLP);

wherein the at least one of the processor or controller is configured to time delivery of the atrial pacing pulse to the atrial chamber, based on timing of a premature ventricular contraction (PVC), in response to a said i2i message received from the vLP indicating that the PVC was detected by the vLP.

10. The aLP of claim 1, further comprising:

one or more receivers configured to receive implant-to-implant (i2i) messages from a ventricular leadless pacemaker (vLP);

wherein the at least one of the processor or controller is configured to disable at least one of the one or more receivers during the ventricular event monitor window to thereby conserve energy.

11. The aLP of claim 1, wherein the at least one of the processor or controller is configured to:

control the pulse generator, or a further pulse generator of the aLP, to selectively generate conductive communication pulses for use in transmitting an implant-to-implant (i2i) message to a ventricular leadless pacemaker (vLP) to inform the vLP of an intrinsic or paced atrial activation, to thereby enable the vLP to time its delivery of a ventricular pacing pulse based on the intrinsic or paced atrial activation; and to include, within the i2i message, a status bit that informs the vLP whether the aLP was able to successfully detect the ventricular activation from the sensed signal during one or more previous cardiac cycles.

12. The aLP of claim 1, wherein the at least one of the processor or controller is configured to:

control the pulse generator, or a further pulse generator of the aLP, to selectively generate conductive communication pulses for use in transmitting an implant-to-implant (i2i) message to a ventricular leadless pacemaker (vLP) to inform the vLP of an intrinsic or paced atrial activation, to thereby enable the vLP to time its delivery of a ventricular pacing pulse based on the intrinsic or paced atrial activation; and to include, within the i2i message, a status bit that informs the vLP whether the aLP received a valid i2i message from the vLP during one or more previous cardiac cycles, thereby enabling the vLP to determine whether to adjust at least one of an amplitude or a timing of one or more further i2i messages that the vLP transmits to the aLP.

13. The aLP of claim 1, wherein to monitor the sensed signal for the ventricular activation within the ventricular event monitor window, the at least one of the processor or controller is configured to at least one of:

determine whether a magnitude associated with one or more features of the sensed signal is above a threshold level within the ventricular event monitor window; or analyze a morphology of one or more features of the sensed signal within the ventricular event monitor window.

14. An implantable system, comprising:
an atrial leadless pacemaker (aLP) configured to be implanted in or on an atrial chamber of a patient's heart; and
a ventricular leadless pacemaker (vLP) configured to be implanted in or on an ventricular chamber of the patient's heart;
the aLP including two or more electrodes;
  a pulse generator electrically coupled or coupleable to at least two of the two or more electrodes;
  at least one of a sensor or circuitry configured to sense a signal from which cardiac activity associated with the ventricular chamber of the patient's heart can be detected based on one or more features of the sensed signal; and
  at least one of a processor or controller configured to specify a ventricular event monitor window;
    monitor the sensed signal for a ventricular activation within the ventricular event monitor window;
    reset an atrial escape interval timer, in response to the ventricular activation being detected from the sensed signal within the ventricular event monitor window; and
    selectively cause an implant-to-implant (i2i) message to be transmitted to the vLP to inform the vLP of an intrinsic or paced atrial activation;
    wherein the atrial escape interval timer is used to time delivery of an atrial pacing pulse to an atrial chamber if an intrinsic atrial activation is not detected within an atrial escape interval; and
the vLP configured to receive the i2i message transmitted by the aLP, and based thereon, time delivery of a ventricular pacing pulse based on the intrinsic or paced atrial activation.

15. The implantable system of claim 14, wherein:
the sensed signal, from which cardiac activity associated with the ventricular chamber of the patient's heart can be detected, comprises an electrogram (EGM); and
the at least one of the processor or controller of the aLP is configured to monitor the EGM for a far-field R-wave or V-pulse within the ventricular event monitor window to thereby monitor for the ventricular activation, which can be intrinsic or paced.

16. The implantable system of claim 14, wherein:
the sensed signal, from which cardiac activity associated with the ventricular chamber of the patient's heart can be detected, is sensed by an accelerometer or a pressure sensor of the aLP; and
the at least one of the processor or controller of the aLP is configured to monitor the sensed signal for a specific heart sound within the ventricular event monitor window, or for an indication of a mechanical contraction within the ventricular event monitor window, to thereby monitor for the ventricular activation, which can be intrinsic or paced.

17. The implantable system of claim 14, wherein:
to specify the ventricular event monitor window, the aLP is configured to start the ventricular event monitor window at a specified atrial-to-ventricular interval minus a specified non-zero delta, after a paced or intrinsic atrial activation; and
the specified atrial-to-ventricular interval comprises one of a PV-interval, a PR-interval, an AV-interval, or an AR-interval.

18. The implantable system of claim 14, wherein to specify the ventricular event monitor window the aLP is configured to:
  detect an end of a P-wave that corresponds to an intrinsic atrial activation; and
  start the ventricular event monitor window at the end of the P-wave or a specified non-zero delta after the end of the P-wave.

19. The implantable system of claim 14, wherein to specify the ventricular event monitor window:
  the aLP uses a ventricular event monitor window start timer to determine when the ventricular event monitor window is to start, such that when the ventricular event monitor window start timer times out the ventricular event monitor window is started; and
  the aLP is configured to start the ventricular event monitor window start timer in one of the following manners:
    when a P-wave is detected by the aLP;
    at an end of the P-wave detected by the aLP;
    at a specified delta after the end of the P-wave detected by the aLP;
    at a peak of the P-wave detected by the aLP;
    at the specified delta after the peak of the P-wave detected by the aLP;
    when a said atrial pacing pulse is delivered by the aLP; or
    at a further specified delta after the said atrial pacing pulse is delivered by the aLP.

20. The implantable system of claim 19, wherein to specify the ventricular event monitor window:
  the aLP uses a ventricular event monitor window timer, which is started when the ventricular event monitor window start timer times out, to determine when the ventricular event monitor window ends.

21. The implantable system of claim 14, wherein the aLP is configured to determine at least one of a start of or a duration of the ventricular event monitor window based on at least one of an atrial cycle length, a measure of temperature, or a measure of activity, so that the at least one of the start of or the duration of the ventricular event monitor window is rate adaptive.

22. The implantable system claim 14, wherein:
  the aLP comprises one or more receivers configured to receive implant-to-implant (i2i) messages from the vLP; and
  the aLP is configured to time delivery of the atrial pacing pulse to the atrial chamber, based on timing of a premature ventricular contraction (PVC), in response to a said i2i message received from the vLP indicating that the PVC was detected by the vLP.

23. The implantable system of claim 14, wherein:
  the aLP comprises one or more receivers configured to receive implant-to-implant (i2i) messages from the vLP; and
  the aLP is configured to disable at least one of the one or more receivers during the ventricular event monitor window to thereby conserve energy.

24. The implantable system of claim 14, wherein the aLP is configured to:
  selectively transmit the i2i message to the vLP to inform the vLP of an intrinsic or paced atrial activation, to thereby enable the vLP to time its delivery of a ventricular pacing pulse based on the intrinsic or paced atrial activation; and
  to include, within the i2i message, a status bit that informs the vLP whether the aLP was able to successfully detect the ventricular activation from the sensed signal during one or more previous cardiac cycles.

25. The implantable system of claim 14, wherein the aLP is configured to:
   selectively transmit the i2i message to the vLP to inform the vLP of an intrinsic or paced atrial activation, to thereby enable the vLP to time its delivery of a ventricular pacing pulse based on the intrinsic or paced atrial activation; and
   to include, within the i2i message, a status bit that informs the vLP whether the aLP received a valid i2i message from the vLP during one or more previous cardiac cycles, thereby enabling the vLP to determine whether to adjust at least one of an amplitude or a timing of one or more further i2i messages that the vLP transmits to the aLP.

26. The implantable system claim 14, wherein to monitor the sensed signal for the ventricular activation within the ventricular event monitor window, the aLP is configured to at least one of:
   determine whether a magnitude associated with one or more features of the sensed signal is above a threshold level within the ventricular event monitor window; or
   analyze a morphology of one or more features of the sensed signal within the ventricular event monitor window.

\* \* \* \* \*